United States Patent [19]

Friebe et al.

[11] 4,346,093
[45] Aug. 24, 1982

[54] HETEROCYCLIC OXYPROPANOLAMINE COMPOUNDS AND PHARMACEUTICAL COMPOSITIONS

[75] Inventors: Walter-Gunar Friebe, Darmstadt; Helmut Michel, Mannheim; Carl H. Ross, Viernheim; Fritz Wiedemann, Weinheim-Lützelsachsen; Wolfgang Bartsch, Viernheim; Karl Dietmann, Mannheim, all of Fed. Rep. of Germany

[73] Assignee: Boehringer.Mannheim GmbH, Mannheim, Fed. Rep. of Germany

[21] Appl. No.: 117,190

[22] Filed: Jan. 31, 1980

[30] Foreign Application Priority Data

Feb. 16, 1979 [DE] Fed. Rep. of Germany ....... 2905877

[51] Int. Cl.³ ..................... A61K 31/41; C07D 249/18
[52] U.S. Cl. .............................. 424/269; 260/326.15; 260/326.13 C; 260/326.16; 424/274; 546/271; 546/273; 548/259; 548/305; 548/371
[58] Field of Search ................. 548/259; 424/274, 269

[56] References Cited

U.S. PATENT DOCUMENTS

| | | | |
|---|---|---|---|
| 3,751,429 | 8/1973 | Seemann et al. ................. | 424/274 |
| 4,140,789 | 2/1979 | Jaeggi et al. ..................... | 424/273 B |
| 4,189,494 | 12/1980 | Engel et al. ........................ | 424/274 |
| 4,215,134 | 7/1980 | Ross et al. ....................... | 424/273 B |
| 4,235,919 | 11/1980 | Berthold ............................ | 424/274 |

*Primary Examiner*—Paul M. Coughlan, Jr.
*Attorney, Agent, or Firm*—Felfe & Lynch

[57] ABSTRACT

The present invention provides heterocyclic oxypropanol derivatives of the general formula:

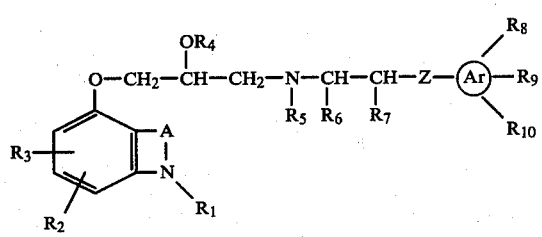

wherein $R_1$ is a hydrogen atom or a lower alkyl, aralkyl or lower alkanoyl radical, $R_2$ and $R_3$, which can be the same or different, are hydrogen atoms or lower alkyl, hydroxyalkyl, alkoxycarbonyl or alkanoyloxyalkyl radicals or together represent an alkylene radical, $R_4$ is a hydrogen atom or a lower alkanoyl radical or an aroyl radical, $R_5$ is a hydrogen atom or a lower alkyl radical or an aralkyl radical, $R_6$ is a hydrogen atom or a lower alkyl radical, $R_7$ is a hydrogen atom, a hydroxyl group or a lower alkyl radical, Z is a valency bond, a methylene radical or an oxygen or sulphur atom, Ar is a carbocyclic aryl radical or a pyridyl radical, $R_8$, $R_9$ and $R_{10}$, which can be the same or different, are hydrogen or halogen atoms, hydroxyl groups, lower alkanoyl radicals, lower alkyl radicals, lower alkenyl radicals, lower alkoxy. radicals, aralkoxy radicals, allyloxy radicals, lower alkylthio radicals, aminocarbonyl radicals, aminosulphonyl radicals or lower alkanoylamino radicals or $R_8$ and $R_9$ together represent a lower alkylenedioxy radical or $R_7$ and $R_8$ together represent a —CH$_2$—O— radical and A is —X$_1$—Y$_1$, in which X$_1$ is a methylene or —NR$_{11}$— radical, R$_{11}$ being a hydrogen atom or a lower alkyl radical, and Y$_1$ is a methylene radical or =C=Q, Q being an oxygen or sulphur atom; or A is —X$_2$=Y$_2$—, in which X$_2$ and Y$_2$, which can be the same or different and signify nitrogen atoms or =C(R$_{12}$)— groups, R$_{12}$ being a hydrogen atom or a lower alkyl or an alkoxycarbonyl radical, and when —X$_2$=Y$_2$— represents a —CH=N— group and R$_1$ is an alkyl or aralkyl radical, because of the ability of indazole to tautomerise, this can also be localized on the nitrogen atom represented by Y$_2$, with the proviso that Y$_1$ or Y$_2$ is joined to =N—R$_1$ in general formula (I), and, when Q is an oxygen atom or —X$_2$=Y$_2$— represents —CR$_{12}$=CR$_{12}$— and Z is a valency bond or when —X$_1$—Y$_1$— represents

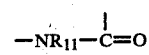

and Z is an oxygen atom or a valency bond, either the two symbols R$_2$ and R$_3$ do not simultaneously represent hydrogen atoms or R$_7$ and R$_8$ together must form a —CH$_2$—O— radical; and the pharmacologically acceptable salts thereof.

The present invention also provides processes for the preparation of these compounds and pharmaceutical compositions containing them.

Furthermore, the present invention is concerned with the use of these compounds for the treatment of cardiac and circulatory diseases.

18 Claims, No Drawings

HETEROCYCLIC OXYPROPANOLAMINE COMPOUNDS AND PHARMACEUTICAL COMPOSITIONS

This invention relates to new heterocyclic oxypropanolamine compounds and to processes for their preparation. In additional aspect, the invention relates to pharmaceutical compositions containing such compounds and to methods for the treatment of cardiac and circulatory diseases utilizing such compounds.

The new heterocyclic oxypropanolamine derivatives according to the present invention are compounds of the formula:

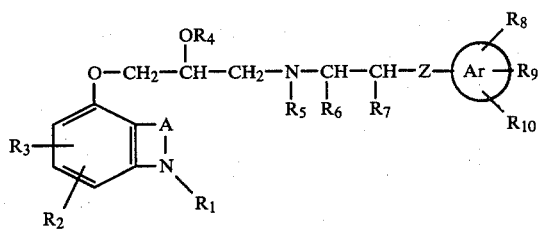

wherein $R_1$ is a hydrogen atom or a lower alkyl, aralkyl or lower alkanoyl radical, $R_2$ and $R_3$, which can be the same or different, are hydrogen atoms or lower alkyl, hydroxyalkyl, alkoxycarbonyl or alkanoyloxyalkyl radicals or together can represent an alkylene radical, $R_4$ is a hydrogen atom, a lower alkanoyl radical or an aroyl radical, $R_5$ is a hydrogen atom or a lower alkyl radical or an aralkyl radical, $R_6$ is a hydrogen atom or a lower alkyl radical, $R_7$ is a hydrogen atom, a hydroxyl group or a lower alkyl radical, Z is a valency bond, a methylene radical or an oxygen or sulphur atom, Ar is a carbocyclic aryl radical or a pyridyl radical, $R_8$, $R_9$ and $R_{10}$, which can be the same or different, are hydrogen or halogen atoms, hydroxyl groups, lower alkanoyl radicals, lower alkyl radicals, lower alkenyl radicals, lower alkoxy radicals, aralkoxy radicals, allyloxy radicals, lower alkylthio radicals, aminocarbonyl radicals, aminosulphonyl radicals or lower alkanoylamino radicals or $R_8$ and $R_9$ together represent a lower alkylenedioxy radical or $R_7$ and $R_8$ together represent a —CH$_2$—O— radical and A is —X$_1$—Y$_1$—, in which X$_1$ is a methylene or —NR$_{11}$ radical, R$_{11}$ being a hydrogen atom or a lower alkyl radical, and Y$_1$ is a methylene radical or =C=Q, Q being an oxygen or sulphur atom, or A is —X$_2$=Y$_2$—, in which X$_2$ and Y$_2$ can be the same or different and signify nitrogen atoms or =C(R$_{12}$)— groups, R$_{12}$ being a hydrogen atom or a lower alkyl or an alkoxycarbonyl radical, and when —X$_2$=Y$_2$— represents a —CH=N— group and R$_1$ represents an alkyl or aralkyl radical, because of the ability of indazoles to tautomerize, this can also be localized on the nitrogen atom represented by Y$_2$, with the proviso that Y$_1$ or Y$_2$ is connected with the group =N—R$_1$ of the general formula (I) and, when Q is an oxygen atom or —X$_2$=Y$_2$— represents —CR$_{12}$=CR$_{12}$— and Z is a valency bond or when —X$_1$—Y$_1$— represents

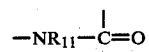

and Z is an oxygen atom or a valency bond, either the two symbols $R_2$ and $R_3$ do not simultaneously represent hydrogen atoms or $R_7$ and $R_8$ together must represent a —CH$_2$—O— radical; and the pharmacologically acceptable salts thereof.

Since the compounds of general formula (I) possess asymmetric carbon atoms, the present invention also provides the optically-active forms and the racemic mixtures of these compounds.

The compounds of general formula (I) and their pharmacologically acceptable salts have a low toxicity and possess outstanding vasodilatory properties which manifest themselves essentially in the lowering of the blood pressure. Furthermore, an inhibition of adrenergic β-receptors is observed. Therefore, the compounds according to the present invention are especially suitable for the treatment and prophylaxis of cardiac and circulatory diseases.

Published Federal Republic of Germany Patent Applications Nos. 19 48 507; 22 30 426; 26 19 164; 26 51 574 and 27 00 193 describe compounds with a similar structure and action. However, by changing the heterocyclic phenolic part, as well as the aminopropoxy side chain, a surprising improvement of action is achieved.

The lower alkyl radicals of the substituents $R_1$, $R_2$, $R_3$, $R_5$, $R_6$, $R_7$, $R_8$, $R_9$, $R_{10}$, $R_{11}$ and $R_{12}$ are to be understood to be straight-chained or branched radicals containing up to 6 and preferably up to 4 carbon atoms, for example, methyl, ethyl, n-propyl, isopropyl, n-butyl, isobutyl, tert.-butyl and n-hexyl radicals, the methyl and ethyl radicals being especially preferred. When $R_2$ and $R_3$ together represent an alkylene radical, this contains 3 or 4 and preferably 3 carbon atoms.

Alkenyl radicals are to be understood to be unsaturated hydrocarbon radicals containing up to 6 carbon atoms, the allyl and methylvinyl radicals being especially preferred.

The hydroxyalkyl radicals of the substituents $R_2$ and $R_3$ contain up to 4 carbon atoms, the 2-hydroxyethyl and the hydroxymethyl radicals being preferred.

The alkoxy radicals of the substituents $R_8$, $R_9$ and $R_{10}$ contain up to 6 and preferably up to 4 carbon atoms, for example the methoxy, ethoxy, propoxy, butoxy or pentoxy radicals, the methoxy, ethoxy and propoxy radicals being preferred.

The alkoxycarbonyl radicals of the substituents $R_2$, $R_3$ and $R_{12}$ are preferably methoxycarbonyl and ethoxycarbonyl radicals.

The alkylthio radicals of the substituents $R_8$, $R_9$ and $R_{10}$ contain up to 6 and preferably up to 4 carbon atoms, the methylthio radical being preferred.

Alkanoyl radicals of the substituents $R_1$, $R_4$, $R_8$, $R_9$ and $R_{10}$, as well as the alkanoyl moieties of the alkanoyloxyalkyl radicals in the definitions of the substituents $R_2$ and $R_3$ and of the alkanoylamino radicals of the substituents $R_8$, $R_9$ and $R_{10}$ contain up to 8 and preferably up to 5 carbon atoms, the alkyl moieties of which can be straight-chained, branched or cyclic, the formyl, acetyl and pivaloyl radicals being preferred. The alkanoyloxyalkyl radicals are preferably alkanoyloxymethyl radicals.

The aroyl radical in the definition of the substituent $R_4$ is preferably the benzoyl radical, which can be substituted one or more times by halogen, alkyl radicals containing up to 4 carbon atoms or alkoxy radicals containing up to 4 carbon atoms.

The aralkyl radical in the definition of the substituents $R_1$ and $R_5$, as well as the aralkoxy radical in the definition of the substituents $R_8$, $R_9$ and $R_{10}$, are to be understood to be radicals which, as the aryl moiety, contain a phenyl or naphthyl radical and, as the alkyl moiety, contain a straight-chained or branched, saturated hydrocarbon chain containing up to 4 carbon atoms, the benzyl radical being preferred.

The carbocyclic radical Ar can be a phenyl or also a naphthyl radical, the phenyl radical being especially preferred.

The lower alkylenedioxy radical jointly formed by $R_8$ and $R_9$ is preferably a methylenedioxy or ethylenedioxy radical.

The symbol A in general formula (I) has, in particular, the meaning that, as heterocycle, there is to be understood the benzimidazolin-2-one, benzimidazolin-2-thione, benzimidazole, benztriazole, indole, indoline or indazole ring system.

Halogen according to the present invention is to be understood to be fluorine, chlorine, bromine or iodine, fluorine, chlorine and bromine being especially preferred.

The new compounds of general formula (I) according. Accordingly ratios of $HD_{50}/DE$-30 mm Hg of approximately 1 are desirable.

(a) a compound of the general formula:

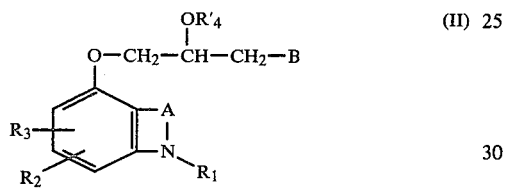

in which $R_1$, $R_2$, $R_3$ and A have the same meanings as above, B is a reactive group and $R_4'$ has the same meaning as $R_4$ or, together with B, represents a valency bond, is reacted with a compound of the general formula:

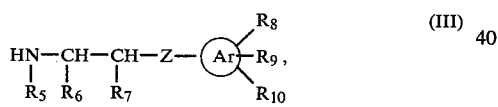

in which $R_5$, $R_6$, $R_7$, $R_8$, $R_9$, $R_{10}$, Z and Ar have the same meanings as above; or (b) a compound of the general formula:

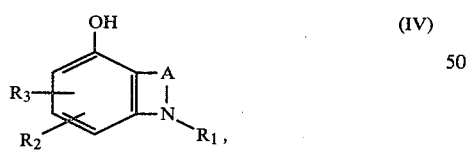

in which $R_1$, $R_2$, $R_3$ and A have the same meaning as above, is reacted with a compound of the general formula:

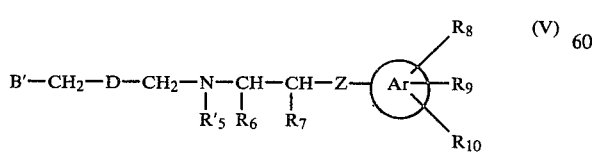

in which $R_6$, $R_7$, $R_8$, $R_9$, $R_{10}$, Z and Ar have the same meanings as above, B' is a reactive group, D is a $=C=O$ or $=CH-OR_4''$ group, $R_4''$ being the same as $R_4$ above or, together with B', representing a valency bond and $R_5'$ has the same meaning as given above for $R_5$ or, together with B', can represent a velency bond, and, when D is a $=C=O$ group, the product obtained is subsequently reduced; or (c) a compound of the general formula:

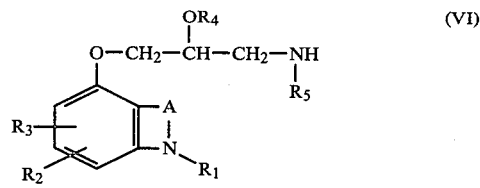

in which $R_1$, $R_2$, $R_3$, $R_4$, $R_5$ and A have the same meanings as above, is reacted with a compound of the general formula:

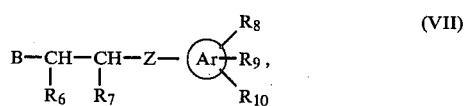

in which B, $R_6$, $R_7$, $R_8$, $R_9$, $R_{10}$, Z and Ar have the same meanings as above; or (d) a mixture of a compound of general formula (VI) with a compound of the general formula:

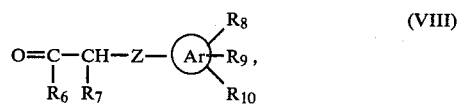

in which $R_6$, $R_8$, $R_9$, $R_{10}$, Z and Ar have the same meanings as above, is hydrogenated; or (e) a compound of general formula (VI) is reacted with a compound of the general formula:

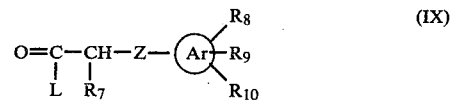

in which $R_7$, $R_8$, $R_9$, $R_{10}$, Z and Ar have the same meanings as above and L is a reactive residue, the amide obtained being subsequently reduced; or (f) a compound of the formula:

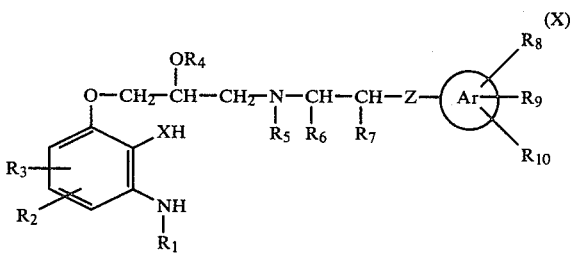

in which $R_1$, $R_2$, $R_3$, $R_4$, $R_5$, $R_6$, $R_7$, $R_8$, $R_9$, $R_{10}$, Z and Ar have the same meanings as above and, when A is to signify $-X_1-Y_1-$, X is $X_1$, is reacted with a compound of the general formula:

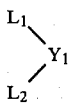
(XIa)

in which $Y_1$ has the same meaning as above, $L_1$ is a hydrogen atom, a hydroxyl group or a reactive residue T and $L_2$ is a hydrogen atom or a reactive residue T, or, when A is to signify $-X_2=Y_2-$, X is $HX_2$, is reacted with a compound of the general formula:

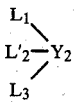
(XIb)

in which $L_1$ and $Y_2$ have the same meanings as above, $L_2'$ is a hydrogen atom or a reactive residue T and $L_3$ is a hydrogen atom or, together with $L_2'$, represents an oxygen atom, and cyclized; or (g) a compound of the general formula:

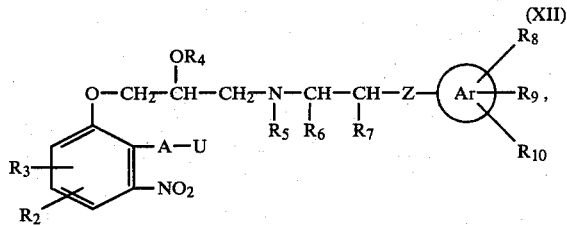
(XII)

in which $R_2$, $R_3$, $R_4$, $R_5$, $R_6$, $R_7$, $R_8$, $R_9$, $R_{10}$, Z, A and Ar have the same meanings as above and U is a group which can be split off, is reduced and cyclized; and subsequently, in a compound obtained of general formula (I), at least one of the substituents $R_1$, $R_2$, $R_3$, $R_4$, $R_5$, $R_8$, $R_9$, $R_{10}$ or $R_{12}$ is, if desired, converted in known manner into another substituent $R_1$, $R_2$, $R_3$, $R_4$, $R_5$, $R_8$, $R_9$, $R_{10}$ or $R_{12}$ as defined above and, if desired, a compound obtained is converted into a pharmacologically acceptable salt.

Reactive residues B in compounds of general formulae (II) and (VII), as well as B' in compounds of general formula (V), are, in particular, acid residues, for example, of hydrohalic acids and sulphonic acids, the chloride, mesyloxy and tosyloxy residues being especially preferred.

Reactive residues L in compounds of general formula (IX) are, in particular, acid residues, for example, of hydrohalic acids or hydrazoic acid or of lower alkyl carboxylic acids, lower alkoxy or aryloxy radicals or amino or imidazolyl radicals, the chloride, azide and imidazolyl residues being especially preferred.

The reactive residues T and U in compounds of general formulae (XIa), (XIb) and (XII) are all residues which can be nucleophilically substituted. Such residues are preferably halogen atoms, for example chlorine or bromine, or amino, imidazolyl, lower alkoxy, lower acyloxy, phenoxy, mercapto or lower alkoxythiocarbonyl radicals. Thus, for example, as compounds of general formula (XIa), there can be used carbonyl halides, urea or N,N'-carbonyldiimidazole, as well as, when Q is a sulphur atom, thiocarbonyl halides, thiourea or xanthogenates. Compounds of general formula (XIa) can also be prepared in situ in the reaction solution from other compounds, for example, carbon disulphide in alkaline solution. As compounds of general formula (XIb), there can be used, for example, carboxylic acids, such as formic acid or acetic acid, carboxylic acid esters or also carboxylic acid halides. However, compounds of general formula (XIb) can also be prepared in situ in the reaction mixture from other compounds, for example, inorganic nitrites in aqueous mineral acids or lower alkyl nitrous acid esters in organic solvents.

The processes according to the present invention are preferably carried out in a solvent which is inert under the reaction conditions, for example, water, methanol, ethanol, n-butanol, dioxan, dimethylformamide or hexamethylphosphoric acid triamide, optionally in the presence of an acid-binding agent. The reactions can also be carried out by mixing the reaction compounds, without the use of solvents. The reactions are carried out at ambient temperature or with heating, optionally under an atmosphere of a protective gas.

When D stands for the group $=C=O$, reduction thereof is preferably carried out by catalytic hydrogenation with noble metal or nickel catalysts or by means of complex metal hydrides, for example sodium borohydride.

The hydrogenation of an amine of general formula (VI) in admixture with a carbonyl compound of general formula (VIII) according to process (d) is carried out in an appropriate solvent, for example methanol, in the presence of a catalyst, for example Raney nickel.

The reduction of the amides obtained according to process (e) can take place with complex metal hydrides, for example lithium aluminium hydride.

The starting materials used in the processes according to the present invention are, as a rule, known from the literature. New compounds are generally obtained analogously to the processes described for the preparation of the known compounds. Thus, for example, amines of general formula (III) can be prepared by reacting haloalkyl nitriles with appropriate phenols, naphthols or aryl compounds, for example by reacting chloroacetonitrile with phenol, and subsequent hydrogenation in the presence of ammonia.

The amines of general formula (VI) can be obtained from the corresponding 2,3-epoxypropoxy derivatives by reaction with liquid ammonia.

Reactive compounds of general formula (VII), for example p-toluenesulphonic acid esters, are, as a rule, prepared from the corresponding phenols, naphthols, aryl or pyridyl compounds by reaction with haloalcohols and subsequent esterification with p-toluenesulphonic acid.

The carbonyl compounds of general formula (VIII) and the reactive acid derivatives of general formula (IX) are obtained, for example, from the corresponding phenols, naphthols, aryl and pyridyl compounds by reaction with appropriate haloalkylcompounds.

The optional conversion of at least one of the substituents $R_1$, $R_2$, $R_3$, $R_4$, $R_5$, $R_8$, $R_9$, $R_{10}$ or $R_{12}$ to be carried out subsequently in compounds of general formula (I) into other substituents $R_1$, $R_2$, $R_3$, $R_4$, $R_5$, $R_8$, $R_9$, $R_{10}$ or $R_{12}$ as defined above can be, for example, the subsequent acylation of a hydroxyl group to give an alkanoyloxy or aroyloxy radical; the reduction of an alkoxycarbonyl radical to a hydroxymethyl radical; the hydrolysis of an alkanoyloxymethyl radical to a hydroxymethyl radical; the reduction of an alkanoyloxymethyl radical to a methyl radical or the splitting off of a benzyl radical or a pivaloyl radical.

When —$OR_4$ is a hydroxyl group, this can be esterified in the usual manner by reaction with an acid halide or acid anhydride, optionally in the presence of an acid-binding agent, for example, pyridine or triethylamine.

The reduction which is optionally to be carried out of compounds of general formula (I), in which $R_2$ and/or $R_3$ is an alkoxycarbonyl or an alkanoyloxymethyl radical, to give compounds of general formula (I), in which $R_2$ and/or $R_3$ is a hydroxymethyl or methyl radical, is preferably carried out by means of complex metal hydrides, for example lithium aluminium hydride, or by catalytic hydrogenation in the presence of noble metal catalysts or Raney nickel.

The hydrolysis of alkanoyloxymethyl radicals $R_2$ and/or in $R_3$ in compounds of general formula (I) to give hydroxymethyl radicals $R_2$ and/or $R_3$ can be carried out in known manner under acidic or alkaline conditions.

The splitting off of a benzyl group represented by $R_1$ and $R_5$ or contained in $R_8$, $R_9$ or $R_{10}$ can be carried out, for example, by hydrogenation in the presence of noble metal catalysts.

For the conversion of compounds of general formula (I) into their pharmacologically acceptable salts, these are preferably reacted in an organic solvent with an inorganic or organic acid, for example, hydrochloric acid, hydrobromic acid, phosphoric acid, sulphuric acid, acetic acid, citric acid, maleic acid or benzoic acid.

The compounds of general formula (I) according to the present invention can be obtained in the form of a racemic mixture. The separation of the racemate into the optically-active forms can be carried out by known methods via the diastereomeric salts. As active acids, there are mainly used tartaric acid, malic acid, camphoric acid and camphorsulphonic acid.

For the preparation of pharmaceutical compositions, the compounds of general formula (I) are mixed in the usual manner with appropriate pharmaceutical carrier materials, aroma, flavoring and coloring materials and formed, for example, into tablets or dragees or, with the addition of appropriate adjuvants, suspended or dissolved in water or in an oil, for example olive oil.

The new compounds of general formula (I) according to the present invention can be administered enterally or parenterally in liquid or solid form. As injection medium, it is preferred to use water which contains the additives conventional in injection solutions, for example, stabilization agents, solubilizing agents or buffers. Additives of this kind include, for example, tartrate and citrate buffers, ethanol, complex formers (such as ethylenediamine-tetraacetic acid and the nontoxic salts thereof) and high molecular weight polymers (such as liquid polyethylene oxide) for viscosity regulation. Solid carrier materials include, for example, starch, lactose, mannitol, methyl cellulose, talc, highly-dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavoring and/or sweetening agents.

The dosage administered depends upon the age, the state of health and the weight of the recipient, the extent of the disease, the nature of other treatments possibly carried out simultaneously, the frequency of the treatment and the nature of the desired action. Usually, the daily dosage of the active compound is 0.1 to 50 mg./kg. of body weight. Normally, 0.5 to 40 and preferably 1.0 to 20 mg./kg./day in one or more administrations per day are effective for the achievement of the desired results.

Besides the compounds set out in the following Examples, the following compounds are also preferred according to the present invention:

4-{2-hydroxy-3-[2-(2,6-dimethoxyphenoxy)-ethylamino]-propoxy}-7-methyl-3-propyl-2-benzimidazolinone 4-{2-hydroxy-3-[2-(2-allyloxyphenoxy)-ethylamino]-propoxy}-6-methylindole 4-{2-hydroxy-3-[2-(2-methylthiophenoxy)-ethylamino]-propoxy}-1-formylindoline 4-{2-hydroxy-3-[2-(2-sulphamylphenoxy)-ethylamino]-propoxy}-indazole 4-{2-hydroxy-3-[2-(3,4-ethylenedioxyphenyl)-ethylamino]-propoxy}-indazole 4-{2-hydroxy-3-[2-(3-ethoxy-4-methoxyphenyl)-ethylamino]-propoxy}-indazole 4-{2-hydroxy-3-[2-(3,4,5-trimethoxyphenyl)-ethylamino]-propoxy}-indazole 4-{2-hydroxy-3-[2-(3-methoxy-4-hydroxyphenyl)-ethylamino]-propoxy}-indazole 4-{2-hydroxy-3-[2-(3-hydroxy-4-n-butoxyphenyl)-ethylamino]-propoxy}-indazole 4-{2-hydroxy-3-[2-(3,4-dihydroxyphenyl)-ethylamino]-propoxy}-indazole 4-{2-hydroxy-3-[3-(3,4-dimethoxyphenyl)-propylamino]-propoxy}-indazole 4-{2-hydroxy-3-[1-(3,4-dimethoxyphenyl)-propyl-2-amino]-propoxy}-indazole 1-methyl-4-{2-hydroxy-3-[2-(3,4-dimethoxyphenyl)-ethylamino]-propoxy}-indazole 1-methyl-4-{2-hydroxy-3-[2-(3,4-dimethoxyphenyl)-ethylamino]-propoxy}-indoline 4-{2-hydroxy-3-[2-(2-methoxyphenylthio)-ethylamino]-propoxy}-1-formylindoline 4-{2-benzoyloxy-3-[2-(3,4-dimethoxyphenyl)-ethylamino]-propoxy}-indazole 4-{2-hydroxy-3-[1-(3,4-dihydroxyphenyl)-2-amino-1-propanol]-propoxy}-6-methylindole.

The following Examples, which are given for the purpose of illustrating the present invention, describe some of the numerous process variations which can be used for the synthesis of the new compounds:

EXAMPLE 1

4-{2-Hydroxy-3-[2-(2-methoxyphenoxy)-propylamino]-propoxy}-7-methyl-2-benzimidazolinone hydrochloride 12.3 g. 2,3-Diamino-1-{2-hydroxy-3-[2-(2-methoxyphenoxy)-propylamino]-propoxy}-4-methylbenzene trihydrochloride are dissolved in 500 ml. water. Phosgene is passed into this solution for 45 minutes at ambient temperature, then flushed with nitrogen and filtered with suction. The crystals so obtained are recrystallized from 300 ml. ethanol/200 ml. methanol, with the addition of active charcoal. There are thus obtained 5.0 g. (46% of theory) 4-{2-hydroxy-3-[2-(2-methoxyphenoxy)-propylamino]-propoxy}-7-methyl-2-benzimidazolinone hydrochloride; m.p. 228°–230° C.

The starting material necessary for the above-described synthesis is prepared as follows:

30.5 g. 2,3-Dinitro-1-(2,3-epoxypropoxy)-4-methylbenzene and 32.6 g. N-benzyl-2-(2-methoxyphenoxy)-propylamine are boiled under reflux for 3 hours in 500 ml. ethanol. The reaction mixture is then hydrogenated in the presence of 10 g. 10% palladium-charcoal in 1 liter ethanol at 50° C. and 30 bar. The catalyst is filtered off and the filtrate is acidified with 2 N hydrochloric acid, clarified with active charcoal and evaporated to dryness. There are obtained 59 g. 2,3-diamino-1-{2-hydroxy-3-[2-(2-methoxyphenoxy)-propylamino]-propoxy}-4-methylbenzene trihydrochloride.

EXAMPLE 2

The following compounds are obtained from phosgene and the appropriately substituted 1-propoxy-2,3-diaminobenzene derivatives in a manner analogous to that described in Example 1:

| designation | Yield % of theory | m.p. °C. (solvent) |
|---|---|---|
| (a) 4-[2-hydroxy-3-(3,4-dimethoxy-phenethylamino)-propoxy]-7-methyl-2-benzimidazolinone hydrochloride from 2,3-diamino-1-[2-hydroxy-3-(3,4-dimethoxyphenethylamino)-propoxy]-4-methyl-benzene trihydrochloride | 42 | 204–206 (isopropanol/ methanol) |
| (b) 4-{2-hydroxy-3-[2-(2-hydroxyphenoxy)-ethylamino]-propoxy}-7-methyl-2-benzimidazolinone hydrochloride from 2,3-diamino-1-{2-hydroxy-3-[2-(2-hydroxyphenoxy)-ethylamino]-propoxy}-4-methyl-benzene trihydrochloride | 67 | 262–263 (methanol/ water) |
| (c) 6,7-dimethyl-4-{2-hydroxy-3-[2-(2-methylphenoxy)-ethylamino]-propoxy}-2-benzimidazolinone hydrochloride from 2,3-diamino-4,5-dimethyl-1-{2-hydroxy-3-[2-(2-methylphenoxy)-ethylamino]-propoxy}-benzene trihydrochloride | 34 | 273–274 (methanol/ water) |
| (d) 4-{2-hydroxy-3-[2-(2-methoxyphenoxy)-ethylamino]-propoxy}-7-methyl-2-benzimidazolinone hydrochloride from 2,3-diamino-1-{2-hydroxy-3-[2-(2-methoxyphenoxy)-ethylamino]-propoxy}-4-methyl-benzene trihydrochloride | 62 | 202–203 (ethanol/ methanol) |
| (e) 4-[2-hydroxy-3-(benzo[b]-1,4-dioxan-2-yl-methylamino)-propoxy]-2-benzimidazolinone hydrochloride from 2,3-diamino-1-[2-hydroxy-3-(benzo[b]-1,4-dioxan-2-yl-methylamino)-propoxy]-benzene trihydrochloride | | |
| (f) 4-[2-hydroxy-3-(2-phenoxy-ethylamino)-propoxy]-7-methyl-2-benzimidazolinone hydrochloride from 2,3-diamino-1-[2-hydroxy-3-(2-phenoxy-ethylamino)-propoxy]-4-methyl-benzene trihydrochloride | 56 | 231–233 (ethanol/ methanol) |
| (g) 4-[2-hydroxy-3-(2-phenoxy-ethylamino)-propoxy]-6-methyl-2-benzimidazolinone hydrochloride from 2,3-diamino-1-[2-hydroxy-3-(2-phenoxyethylamino)-propoxy]-5-methyl-benzene trihydrochloride | 52 | 250–252 (ethanol/ methanol) |
| (h) 4-{2-hydroxy-3-[2-(2-methoxyphenoxy)-ethylamino]-propoxy}-6-methyl-2-benzimidazolinone hydrochloride from 2,3-diamino-1-{2-hydroxy-3-[2-(2-methoxyphenoxy)-ethylamino]-propoxy}-5-methyl-benzene trihydrochloride | 87 | 213–215 (ethanol) |
| (i) 4-[2-hydroxy-3-(3,4-dimethoxyphenethylamino)-propoxy]-6-methyl-2-benzimidazolinone hydrochloride from 2,3-diamino-1-[2-hydroxy-3-(3,4-dimethoxyphenethylamino)-propoxy]-5-methyl-benzene trihydrochloride | 15 | 260–262 (ethanol) |
| (j) 4-{2-hydroxy-3-[2-(2-allyloxyphenoxy)-ethylamino]-propoxy}-7-methyl-2-benzimidazolinone hydrochloride from 2,3-diamino-1-{2-hydroxy-3-[2-(2-allyloxyphenoxy)-ethylamino]-propoxy}-4-methyl-benzene trihydrochloride | | |

EXAMPLE 3

4-{2-Hydroxy-3-[2-(2-methoxyphenoxy)-propylamino]-propoxy}-7-methylbenzimidazole hydrochloride 14.7 g. 2,3-Diamino-1-{2-hydroxy-3-[2-(2-methoxyphenoxy)-propylamino]-propoxy}-4-methylbenzene trihydrochloride are boiled under reflux for 3 hours in 80 ml. formic acid. The reaction mixture is then clarified with active charcoal and evaporated to dryness. The resultant formyl compound is saponified in 50 ml. 2 N hydrochloric acid at boiling temperature. After evaporating to dryness, the residue is recrystallized from 50 ml. ethanol, with the addition of active charcoal. There are obtained 5.6 g. (41% of theory) 4-{2-hydroxy-3-[2-(2-methoxyphenoxy)-propylamino]-propoxy}-7-methylbenzimidazole hydrochloride; m.p. 103°–105° C.

EXAMPLE 4

The following compounds are obtained from formic acid and the appropriately substituted 1-propoxy-2,3-diaminobenzene derivatives in a manner analogous to that described in Example 3:

| designation | Yield % of theory | m.p. °C. (solvent) |
|---|---|---|
| (a) 4-[2-hydroxy-3-(3,4-dimethoxyphenethylamino)-propoxy]-benzimidazole hydrochloride from 2,3-diamino-1-[2-hydroxy-3-(3,4-dimethoxyphenethylamino)-propoxy]-benzene trihydrochloride | 50 | 255–256 (ethanol) |
| (b) 4-[2-hydroxy-3-(3,4-dimethoxyphenethylamino)-propoxy]-7-methylbenzimidazole hydrochloride from 2,3-diamino-1-[2-hydroxy-3-(3,4-dimethoxyphenethylamino)-propoxy]-4-methyl-benzene trihydrochloride | 20 | 254–256 (ethanol/ water) |
| (c) 4-{2-hydroxy-3-[2-(2-hydroxy- | | |

-continued

| designation | Yield % of theory | m.p. °C. (solvent) |
|---|---|---|
| phenoxy)-ethylamino]-propoxy}-7-methylbenzimidazole hydrochloride from 2,3-diamino-1-{2-hydroxy-3-[2-(2-hydroxyphenoxy)-ethylamino]-propoxy}-4-methylbenzene trihydrochloride | 92 | 229–231 (water) |
| (d) 6,7-dimethyl-4-{2-hydroxy-3-[2-(2-methylphenoxy)-ethylamino]-propoxy}-benzimidazole hydrochloride from 2,3-diamino-4,5-dimethyl-1-{2-hydroxy-3-[2-(2-methylphenoxy)-ethylamino]-propoxy}-benzene trihydrochloride | 17 | 106–109 (ethanol/ ethyl acetate) |
| (e) 4-{2-hydroxy-3-[2-(2-methoxyphenoxy)-ethylamino]-propoxy}-7-methylbenzimidazole hydrochloride from 2,3-diamino-1-{2-hydroxy-3-[2-(2-methoxyphenoxy)-ethylamino]-propoxy}-4-methylbenzene trihydrochloride | 62 | 219–221 (ethanol/ methanol) |
| (f) 4-{-2-hydroxy-3-[2-(2-methoxyphenoxy)-ethylamino]-propoxy}-benzimidazole hydrochloride from 2,3-diamino-1-{2-hydroxy-3-[2-(2-methoxyphenoxy)-ethylamino]-propoxy}-benzene trihydrochloride | 17 | 115–118 (ethanol) |
| (g) 4-[2-hydroxy-3-(4-phenyl-2-butylamino)-propoxy]-benzimidazole hydrochloride from 2,3-diamino-1-[2-hydroxy-3-(4-phenyl-2-butylamino)-propoxy]-benzene trihydrochloride | 77 | amorphous |
| (h) 4-[2-hydroxy-3-(2-phenoxy-ethylamino)-propoxy]-benzimidazole hydrochloride from 2,3-diamino-1-[2-hydroxy-3-(2-phenoxyethylamino)-propoxy]-benzene trihydrochloride | 10 | amorphous |
| (i) 4-[2-hydroxy-3-(benzo[b]-1,4-dioxan-2-yl-methylamino)-propoxy]-benzimidazole hydrochloride from 2,3-diamino-1-[2-hydroxy-3-(benzo[b]-1,4-dioxan-2-yl-methylamino)-propoxy]-benzene trihydrochloride | 19 | 105–107 (isopropanol/ methanol) |
| (j) 4-{2-hydroxy-3-[2-(2-methoxyphenoxy)-propylamino]-propoxy}-benzimidazole hydrochloride from 2,3-diamino-1-{2-hydroxy-3-[2-(2-methoxyphenoxy)-propylamino]-propoxy}-benzene trihydrochloride | 59 | 115–118 (ethanol) |

EXAMPLE 5

4-[2-Hydroxy-3-(3,4-dimethoxyphenethylamino)-propoxy]-2,7-dimethylbenzimidazole hydrochloride 14.6 g. 2,3-Diamino-1-[2-hydroxy-3-(3,4-dimethoxyphenethylamino)-propoxy]-4-methylbenzene trihydrochloride are heated under reflux for 3 hours in 50 ml. glacial acetic acid. The reaction mixture is then clarified with active charcoal and completely evaporated. The residue is boiled under reflux for 2 hours in 40 ml. 2 N hydrochloric acid and subsequently evaporated to dryness. The residue is purified over a column of silica gel, using chloroform/methanol (8:2 v/v) as elution agent. The eluate is evaporated to dryness and thereafter recrystallised from 100 ml. ethanol to give 2.2 g. (19% of theory) 4-[2-hydroxy-3-(3,4-dimethoxyphenethylamino)-propoxy]-2,7-dimethylbenzimidazole hydrochloride; m.p. 167°–169° C.

The starting material used in the above described synthesis is prepared as follows:

26.0 g. N-Benzyl-3,4-dimethoxyphenethylamine and 24.3 g. 2,3-dinitro-1-(2,3-epoxypropoxy)-4-methylbenzene are boiled under reflux for 4 hours in 300 ml. ethanol. The reaction mixture is then diluted with 300 ml. ethanol and hydrogenated at 50° C. and 30 bar pressure in the presence of 7.0 g. 10% palladium-charcoal. The catalyst is filtered off, the filtrate is acidified with 2 N hydrochloric acid and then evaporated to give the desired amorphous diamine salt.

EXAMPLE 6

From acetic acid and the appropriately substituted 1-propoxy-2,3-diaminobenzene derivatives, there are obtained the following compounds in a manner analogous to that described in Example 5:

| Designation | Yield % of theory | m.p. °C. (solvent) |
|---|---|---|
| (a) 4-{2-hydroxy-3-[2-(2-propoxyphenoxy)-ethylamino]-propoxy}-2,7-dimethylbenzimidazole hydrochloride from 2,3-diamino-4-methyl-1-{2-hydroxy-3-[2-(2-propoxyphenoxy)-ethylamino]-propoxy}-benzene trihydrochloride | 44 | 143–145 (ethanol/ ethyl acetate) |
| (b) 4-{2-hydroxy-3-[2-(2-methoxy-4-methylphenoxy)-ethylamino]-propoxy}-2,7-dimethylbenzimidazole hydrochloride from 2,3-diamino-4-methyl-1-{2-hydroxy-3-[2-(2-methoxy-4-methylphenoxy)-ethylamino]-propoxy}-benzene trihydrochloride | 62 | 165–167 (ethanol) |

EXAMPLE 7

4-[2-Hydroxy-3-(3,4-dimethoxyphenethylamino)-propoxy]-benzotriazole hydrochloride 14.1 g. 2,3-Diamino-1-[2-hydroxy-3-(3,4-dimethoxyphenethylamino)-propoxy]-benzene trihydrochloride are dissolved in 10 ml. water and 3.5 ml. glacial acetic acid, cooled to 5° C. and mixed with 2.07 g. sodium nitrite in 3.6 ml. water. The reaction mixture is then stirred for 2.5 hours at ambient temperature. The resultant sodium chloride is precipitated out by the addition of 480 ml. isopropanol. After filtration, the filtrate is evaporated, purified over a column of silica gel using methanol/ethyl acetate (2:1 v/v) as elution agent, mixed with ethereal hydrochloric acid and the hydrochloride so obtained is crystallized from ethanol. There are obtained 1.26 g. (10% of theory) 4-[2-hydroxy-3-(3,4-dimethoxyphenethylamino)-propoxy]-benzotriazole hydrochloride; m.p. 123°–124° C.

EXAMPLE 8

From sodium nitrite and the appropriately substituted 1-propoxy-2,3-diaminobenzene derivatives, there are obtained the following compounds in a manner analogous to that described in Example 7:

| designation | Yield % of theory | m.p. °C. (solvent) |
|---|---|---|
| (a) 4-[2-hydroxy-3-(3,4-dimethoxy-phenethylamino)-propoxy]-7-methylbenzotriazole hydrochloride from 2,3-diamino-1-[2-hydroxy-3-(3,4-dimethoxyphenethylamino)-propoxy]-4-methylbenzene trihydrochloride | 16 | 184–186 (isopropanol) |
| (b) 4-{2-hydroxy-3-[2-(2-methoxyphenoxy)-ethylamino]-propoxy}-benzotriazole hydrochloride from 2,3-diamino-1-{2-hydroxy-3-[2-(2-methoxyphenoxy)-ethylamino]-propoxy}-benzene trihydrochloride | 25 | 113–115 (methanol/ diethyl ether) |
| (c) 4-{2-hydroxy-3-[2-(2-methoxyphenoxy)-ethylamino]-propoxy}-7-methylbenzotriazole hydrochloride from 2,3-diamino-1-{2-hydroxy-3-[2-(2-methoxyphenoxy)-ethylamino]-propoxy}-4-methylbenzene trihydrochloride | 48 | 109–111 (isopropanol/ methanol) |
| (d) 4-{2-hydroxy-3-[2-(2-hydroxyphenoxy)-ethylamino]-propoxy}-benzotriazole hydrochloride from 2,3-diamino-1-{2-hydroxy-3-[2-(2-hydroxyphenoxy)-ethylamino]-propoxy}-benzene trihydrochloride | 14 | 200–203 (ethanol/ methanol) |
| (e) 4-[2-hydroxy-3-(2-methoxyphenethylamino)-propoxy]-benzotriazole hydrochloride from 2,3-diamino-1-[2-hydroxy-3-(2-methoxyphenethylamino)-propoxy]-benzene trihydrochloride | 21 | 82–85 (ethanol/ ethyl acetate) |
| (f) 4-{2-hydroxy-3-[2-(2-methoxyphenoxy)-propylamino]-propoxy}-benzotriazole hydrochloride from 2,3-diamino-1-{2-hydroxy-3-[2-(2-methoxyphenoxy)-propylamino]-propoxy}-benzene trihydrochloride | 62 | amorphous |
| (g) 4-{2-hydroxy-3-[2-(2-allyloxyphenoxy)-propylamino]-propoxy-benzotriazole hydrochloride from 2,3-diamino-1-{2-hydroxy-3-[2-(2-allyloxyphenoxy)-propylamino]-propoxy}-benzene trihydrochloride | | |

EXAMPLE 9

4-[2-Hydroxy-3-(3,4-dimethoxyphenethylamino)-propoxy]-benzimidazoline-2-thione hydrochloride 17.4 g. 2,3-Diamino-1-[2-hydroxy-3-(3,4-dimethoxyphenethylamino)-propoxy]-benzene trihydrochloride are dissolved in 450 ml. chloroform and 50 ml. ethanol and mixed dropwise at ambient temperature with 3.2 ml. thiophosgene in 30 ml. chloroform. After 2 hours, the reaction mixture is treated with active charcoal and then evaporated to dryness. The residue is purified over a column of silica gel, using chloroform/methanol (8:2 v/v) as elution agent, to give 10 g. (62% of theory) of uniform product. After taking up in isopropanol and mixing with ethereal hydrochloric acid, followed by precipitation by the addition of ethyl acetate, there is obtained 4-[2-hydroxy-3-(3,4-dimethoxyphenethylamino)propoxy]-benzimidazoline-2-thione hydrochloride; m.p. 108°–110° C.

EXAMPLE 10

The following compounds are obtained from thiophosgene and the appropriately substituted 1-propoxy-2,3-diaminobenzene derivative in a manner analogous to that described in Example 9:

| designation | Yield % of theory | m.p. °C. (solvent) |
|---|---|---|
| (a) 4-[2-hydroxy-3-(3,4-dimethoxyphenethylamino)-propoxy]-7-methyl-benzimidazoline-2-thione hydrochloride from 2,3-diamino-1-[2-hydroxy-3-(3,4-dimethoxyphenethylamino)-propoxy]-4-methylbenzene trihydrochloride | | |
| (b) 4-{2-hydroxy-3-[2-(2-methoxyphenoxy)-propylamino]-propoxy}-7-methyl-benzimidazoline-2-thione benzoate from 2,3-diamino-1-{2-hydroxy-3-[2-(2-methoxyphenoxy)-propylamino]-propoxy}-4-methylbenzene trihydrochloride | 14 | 169–170 (ethanol/ diethyl ether) |
| (c) 4-{2-hydroxy-3-[2-(2-methylphenoxy)-ethylamino]-propoxy}-benzimidazoline-2-thione hydrochloride from 2,3-diamino-1-{2-hydroxy-3-[2-(2-methylphenoxy)-ethylamino]-propoxy}-benzene trihydrochloride | | |

EXAMPLE 11

4-{2-Hydroxy-3-[2-(2-hydroxyphenoxy)-ethylamino]-propoxy}-6,7-cyclopentenobenzimidazolin-2-one hydrochloride Phosgene is passed for 1 hour into a solution of 6.5 g. (0.0175 mol) 4,5-diamino-6-{2-hydroxy-3-[2-(2-hydroxyphenoxy)-ethylamino]-propoxy}-indane hydrochloride in 250 ml. water and 100 ml. tetrahydrofuran. The reaction mixture is then thoroughly flushed with nitrogen, filtered and the solid precipitate thereby obtained taken up in a dilute aqueous solution of sodium hydroxide. The solution is washed with methylene chloride, the aqueous phase is adjusted to pH 7, extracted with methylene chloride and evaporated and the residue is taken up in acetone, the desired hydrchloride being precipitated out with ethereal hydrochloric acid. There are obtained 2.8 g. (36% of theory) 4-{2-hydroxy-3-[2-(2-hydroxyphenoxy)-ethylamino]-propoxy}-6,7-cyclopentenobenzimidazolin-2-one hydrochloride in the form of an amorphous salt; m.p. 145°–155° C.

The diamino compound used as starting material can be prepared in the following manner:

The condensation of 5-amino-6-(2,3-epoxypropoxy)-4-nitroindane and N-benzyl-2-(2-benzyloxyphenoxy)-ethylamine gives 5-amino-6-{3-[N-benzyl-2-(2-benzyloxyphenoxy)-ethylamino]-2-hydroxypropoxy}-4-nitroindane in the form of an oil. This compound, in the form of its hydrochloride, is hydrogenated and hydrogenolytically debenzylated in methanolic solution in the presence of 10% palladium-charcoal to give 4,5-diamino-6-{2-hydroxy-3-[2-(2-hydroxyphenoxy)-ethylamino]-propoxy}-indane hydrochloride; m.p. 193°–195° C.

EXAMPLE 12

4-{3-[2-(3,4-dimethoxyphenyl)-ethylamino]-2-hydroxypropoxy}-6,7-cyclopentenobenzimidazolin-2-one hydrochloride In a manner analogous to that described in Example 1, from phosgene and 4,5-diamino-6-{3-[2-(3,4-dimethoxyphenyl)-ethylamino]-2-hydroxypropoxy}-indane hydrochloride, there is obtained 4-{3-[2-(3,4-dimethoxyphenyl)-ethylamino]-2-hydroxypropoxy}-6,7-cyclopentenobenzimidazolin-2-one hydrochloride; m.p. 193°-195° C.

The diamine compound used as starting material can be prepared in the following manner:

By reaction of 5-amino-6-(2,3-epoxypropoxy)-4-nitroindane with 3,4-dimethoxyphenethylamine, there is obtained 5-amino-6-{3-[2-(3,4-dimethoxyphenyl)-ethylamino]-2-hydroxypropoxy}-4-nitroindane hydrochloride; m.p. 230°-236° C. Hydrogenation of this compound in methanolic solution in the presence of platinum dioxide gives 4,5-diamino-6-{3-[2-(3,4-dimethoxyphenyl)-ethylamino]-2-hydroxypropoxy}-indane, which is isolated as the amorphous hydrochloride.

EXAMPLE 13

4-[2-Hydroxy-3-(2-phenoxypropylamino)-propoxy]-6,7-cyclopentenobenzimidazolin-2-one hydrochloride In a manner analogous to that described in Example 1, from phosgene and 4,5-diamino-6-[2-hydroxy-3-(2-phenoxypropylamino)-propoxy]-indane hydrochloride, there is obtained 4-[2-hydroxy-3-(2-phenoxypropylamino)-propoxy]-6,7-cyclopentenobenzimidazolin-2-one hydrochloride; m.p. 261°-263° C.

The diamino compound used as starting material can be prepared as follows:

The condensation of 5-amino-6-(2,3-epoxypropoxy)-4-nitroindane and N-benzyl-2-phenoxypropylamine gives 5-amino-6-[3-(N-benzyl-2-phenoxypropylamino)-2-hydroxypropoxy]-4-nitroindane in the form of an amorphous hydrochloride; m.p. 70°-80° C. By hydrogenation and hydrogenolytic debenzylation of this compound in methanolic solution over 10% palladium-charcoal, there is obtained 4,5-diamino-6-[2-hydroxy-3-(2-phenoxypropylamino)-propoxy]-indane hydrochloride; m.p. 153°-155° C.

EXAMPLE 14

4-{2-Hydroxy-3-[2-(2-hydroxyphenoxy)-ethylamino]-propoxy}-6,7-cyclopentenobenzimidazole A mixture of 4.1 g. (0.01 mol) 4,5-diamino-6-{2-hydroxy-3-[2-(2-hydroxyphenoxy)-ethylamino]-propoxy}-indane hydrochloride and 35 ml. formamide is heated under reflux for 40 minutes, then evaporated and the residue mixed with water, extracted with methylene chloride, the extract evaporated and the residue triturated with ethyl acetate. There is obtained 1.3 g. 4-{2-hydroxy-3-[2-(2-hydroxyphenoxy)-ethylamino]-propoxy}-6,7-cyclopentenobenzimidazole; m.p. 182°-183° C.

EXAMPLE 15

4-{2-Hydroxy-3-[(1-methyl-3-phenyl)-propylamino]-propoxy}-6-methylindole benzoate 4.9 g. 4-(2,3-Epoxypropoxy)-6-methylindole (see published Federal Republic of Germany Patent Application No. 25 08 251) and 3.7 g. (1-methyl-3-phenyl)-propylamine are stirred for 18 hours in 50 ml. n-butanol, evaporated in a vacuum and the residue shaken up with 1 N lactic acid and diethyl ether. After precipitation of the base with dilute aqueous sodium hydroxide solution, it is extracted with diethyl ether/ethyl acetate (1:1 v/v) and purified chromatographically over silica gel with methylene chloride/methanol (9:1 v/v). The base obtained is dissolved in ethyl acetate, mixed with an equivalent amount of benzoic acid and filtered off with suction. There are obtained 2.0 g. (18% of theory) 4-{2-hydroxy-3-[(1-methyl-3-phenyl)-propylamino]-propoxy}-6-methylindole benzoate; m.p. 119°-122° C.

EXAMPLE 16

The following compounds are obtained in a manner analogous to that described in Example 15:

| designation | Yield % of theory | m.p. °C. (solvent) |
| --- | --- | --- |
| (a) 4-{2-hydroxy-3-[2-(3,4-dimethoxyphenyl)-ethylamino]-propoxy}-6-methylindole benzoate from 4-(2,3-epoxypropoxy)-6-methylindole and 2-(3,4-dimethoxyphenyl)-ethylamine | 27 | 147–148 (ethyl acetate) |
| (b) 4-{2-hydroxy-3-[2-(2-pyridinyl)-ethylamino]-propoxy}-6-methylindole di-p-nitrobenzoate from 4-(2,3-epoxypropoxy)-6-methylindole and 2-(2-pyridinyl)-ethylamine | 16 | 146 (methanol) |
| (c) 4-[2-hydroxy-3-(2-phenoxyethylamino)-propoxy]-6-methyl-indole benzoate from 4-(2,3-epoxypropoxy)-6-methylindole and 2-phenoxyethylamine | 16 | 123–125 (diethyl ether) |
| (d) 4-{2-hydroxy-3-[(1-methyl-2-phenyl)-ethylamino]-propoxy}-6-methylindole benzoate from 4-(2,3-epoxypropoxy)-6-methylindole and (1-methyl-2-phenyl)-ethylamine | 20 | 125–128 (ethyl acetate) |
| (e) 4-{2-hydroxy-3-[2-(2-methoxyphenoxy)-ethylamino]-propoxy}-6-methylindole from 4-(2,3-epoxypropoxy)-6-methylindole and 2-(2-methoxyphenoxy)-ethylamine | 19 | 123–125 (ethyl acetate) |
| (f) 4-{2-hydroxy-3-[2-(4-carbamidophenoxy)-ethylamino]-propoxy}-6-methylindole from 4-(2,3-epoxypropoxy)-6-methylindole and 2-(4-carbamidophenoxy)-ethylamine | 19 | 128–130 (methanol) |
| (g) 4-[2-hydroxy-3-(benzo[b]-1,4-dioxan-2-yl-methylamino)-propoxy]-6-methylindole p-chlorobenzoate from 4-(2,3-epoxypropoxy)-6-methylindole and 2-(aminomethyl)-1,4-benzo[b]-dioxan | 14 | 168–170 (ethyl acetate) |
| (h) 4-[2-hydroxy-3-(2-phenoxy-N-benzylpropylamino)-propoxy]-6-methylindole from 4-(2,3-epoxypropoxy)-6-methylindole and 2-phenoxy-N-benzylpropylamine | 95 | oil |
| (i) 4-{2-hydroxy-3-[2-(2-methoxyphenoxy)-N-benzylpropylamino]-propoxy}-6-methylindole from 4-(2,3-epoxypropoxy)-6-methylindole and 2-(2-methoxyphenoxy)- | 95 | oil |

-continued

| designation | Yield % of theory | m.p. °C. (solvent) |
|---|---|---|
| N-benzylpropylamine | | |
| (j) 4-{2-hydroxy-3-[2-(5-carbamido-2-pyridoxy)-N-benzylethylamino]-propoxy}-6-methylindole from 4-(2,3-epoxypropoxy)-6-methyl-indole and 2-(5-carbamido-2-pyridoxy)-N-benzylethylamine | 76 | oil |
| (k) 4-{2-hydroxy-3-[2-(2-benzyloxy-phenoxy)-ethylamino]-propoxy}-6-methylindole from 4-(2,3-epoxypropoxy)-6-methyl-indole and 2-(2-benzyloxyphenoxy)-ethylamine | 16 | oil |
| (l) 4-{2-hydroxy-3-[2-(3,4-dimethoxy-phenyl)-ethylamino]-propoxy}-6-methoxycarbonylindole from 4-(2,3-epoxypropoxy)-6-methoxy-carbonylindole and 2-(3,4-dimethoxyphenyl)-ethylamine | 59 | 145–147 (isopropanol/ diethyl ether) |
| (m) 4-{2-hydroxy-3-[2-(3,4-dimethoxy-phenyl)-ethylamino]-propoxy}-6-hydroxymethylindole from 4-(2,3-epoxypropoxy)-6-hydroxy-methylindole and 2-(3,4-dimethoxy-phenyl)-ethylamine | 35 | 60 amorphous |
| (n) 4-{2-hydroxy-3-[2-(2-allyloxy-phenoxy)-ethylamino]-propoxy}-6-methylindole from 4-(2,3-epoxypropoxy)-6-methyl-indole and 2-(allyloxyphenoxy)-ethylamine | 36 | 125 (methanol) |

EXAMPLE 17

4-[2-Hydroxy-3-(2-phenoxypropylamino)-propoxy]-6-methylindole p-chlorobenzoate 8 g. 4-[2-Hydroxy-3-(2-phenoxy-N-benzylpropylamino)-propoxy]-6-methyl indole (preparation see Example 16h) in 200 ml. methanol and 5 ml. triethylamine are hydrogenated at ambient temperature and 1 bar hydrogen pressure in the presence of 2 g. 10% palladium-charcoal, filtered, the filtrate evaporated and the residue dissolved in 50 ml. ethyl acetate and then mixed with the calculated amount of p-chlorobenzoic acid. After filtering off the product thus obtained and recrystallizing it, there are obtained 4.3 g. (42% of theory) 4-[2-hydroxy-3-(2-phenoxypropylamino)-propoxy]-6-methylindole p-chlorobenzoate; m.p. 134°–136° C.

EXAMPLE 18

The following compounds are obtained in a manner analogous to that described in Example 17:

| designation | Yield % of theory | m.p. °C. (solvent) |
|---|---|---|
| (a) 4-{2-hydroxy-3-[2-(2-methoxy-phenoxy)-propylamino]-propoxy}-6-methylindole from 4-{2-hydroxy-3-[2-(2-methoxy-phenoxy)-N-benzylpropylamino]-propoxy}-6-methylindole (see Example 16i) | 58 | 104–106 (ethyl acetate) |
| (b) 4-{2-hydroxy-3-[2-(5-carbamido-2-pyridoxy)-ethylamino]-propoxy}- | | |
| 6-methylindole di-p-chloro-benzoate from 4-{2-hydroxy-3-[2-(5-carbamido-2-pyridoxy)-N-benzylethylamino]-propoxy}-6-methylindole (see Example 16j) | 10 | 141–143 (isopropanol) |
| (c) 4-{2-hydroxy-3-[2-(2-hydroxy-phenoxy)-ethylamino]-propoxy}-6-methylindole benzoate from 4-{2-hydroxy-3-[2-(2-benzyloxy-phenoxy)-ethylamino]-propoxy}-6-methylindole (see Example 16k) | 72 | 85–90 (methanol) |

EXAMPLE 19

4-{2-Hydroxy-3-[2-(3,4-dimethoxyphenyl)-ethylamino]-propoxy}-6-hydroxymethylindole A solution of 5.0 g. 4-{2-hydroxy-3-[2-(3,4-dimethoxyphenyl)-ethylamino]-propoxy}-6-methoxycarbonylindole (preparation see Example 16l) in 150 ml. anhydrous tetrahydrofuran is added dropwise to a suspension of 2.3 g. lithium aluminium hydride in 50 ml. anhydrous tetrahydrofuran, followed by stirring for 12 hours at ambient temperature, decomposition, while cooling, with an aqueous solution of sodium chloride and 10 N aqueous sodium hydroxide solution, filtration and then washing with tetrahydrofuran and evaporation. The residue is purified over a column of silica gel, using methylene chloride/methanol (9:1 v/v) as elution agent. The base is precipitated out with diethyl ether and filtered off with suction. There are obtained 2.4 g. (51% of theory) 4-{2-hydroxy-3-[2-(3,4-dimethoxyphenyl)-ethylamino]propoxy}-6-hydroxymethylindole, which sinters at 60° C.

EXAMPLE 20

2-Ethoxycarbonyl-4-[2-hydroxy-3-(3-phenylpropylamino)-propoxy]-6-methylindole 3.6 g. 2-Ethoxycarbonyl-4-(2,3-epoxypropoxy)-6-methylindole (see published Federal Republic of Germany Patent Application No. 26 26 890) and 1.76 g. 3-phenylpropylamine are stirred at ambient temperature in 5 ml. hexamethylphosphoric acid triamide until the reaction is complete. The reaction mixture is then taken up in water and diethyl ether, the ethereal phase is extracted with 1 N tartaric acid and the base liberated by the addition of aqueous potassium carbonate solution. After shaking out with diethyl ether, drying and evaporating, there are obtained 2.0 g. (33% of theory) 2-ethoxycarbonyl-4-[2-hydroxy-3-(3-phenylpropylamino)-propoxy]-6-methylindole; m.p. 127° C.

The acetate is prepared as follows: 1.4 g. 2-ethoxycarbonyl-4-[2-hydroxy-3-(3-phenylpropylamino)-propoxy]-6-methylindole are dissolved in 10 ml. ethyl acetate with gentle warming, then mixed with 0.2 ml. acetic acid and, after cooling, filtered with suction. There is obtained 1.3 g. 2-ethoxycarbonyl-4-[2-hydroxy-3-(3-phenylpropylamino)-propoxy]-6-methylindole acetate; m.p. 155° C.

EXAMPLE 21

The following compounds are obtained in a manner analogous to that described in Example 20:

| designation | Yield % of theory | m.p. °C. (solvent) |
|---|---|---|
| (a) 2-ethoxycarbonyl-4-{2-hydroxy-3-[(1-methyl-3-phenyl)-propyl-amino]-propoxy}-6-methylindole from 2-ethoxycarbonyl-4-(2,3-epoxy-propoxy)-6-methylindole and (1-methyl-3-phenyl)-propylamine | 28 | 133–134 (ethyl acetate) |
| (b) 2-ethoxycarbonyl-4-{2-hydroxy-3-[2-(2-pyridinyl)-ethylamino]-propoxy}-6-methylindole benzoate from 2-ethoxycarbonyl-4-(2,3-epoxy-propoxy)-6-methylindole and 2-(2-pyridinyl)-ethylamine | 20 | 129–131 (ethyl acetate) |
| (c) 2-ethoxycarbonyl-4-{2-hydroxy-3-[2-(4-pyridinyl)-ethylamino]-propoxy}-6-methylindole from 2-ethoxycarbonyl-4-(2,3-epoxy-propoxy)-6-methylindole and 2-(4-pyridinyl)-ethylamine | 32 | 133–134 (diethyl ether) |
| (d) 2-ethoxycarbonyl-4-[2-hydroxy-3-(2-phenoxyethylamino)-propoxy]-6-methylindole benzoate from 2-ethoxycarbonyl-4-(2,3-epoxy-propoxy)-6-methylindole and 2-phenoxyethylamine | 24 | 147 (ethyl acetate) |
| (e) 2-ethoxycarbonyl-4-{2-hydroxy-3-[(1-methyl-2-phenoxy)-ethylamino]-propoxy}-6-methylindole benzoate from 2-ethoxycarbonyl-4-(2,3-epoxy-propoxy)-6-methylindole and 1-methyl-2-phenoxyethylamine | 23 | 135–137 (diethyl ether) |
| (f) 2-ethoxycarbonyl-4-{2-hydroxy-3-[2-(2-methoxyphenoxy)-ethylamino]-propoxy}-6-methylindole from 2-ethoxycarbonyl-4-(2,3-epoxy-propoxy)-6-methylindole and 2-(2-methoxyphenoxy)-ethylamine | 21 | 145–147 (ethyl acetate) |
| (g) 2-ethoxycarbonyl-4-{2-hydroxy-3-[2-(4-carbamidophenoxy)-ethyl-amino]-propoxy}-6-methylindole acetate from 2-ethoxycarbonyl-4-(2,3-epoxy-propoxy)-6-methylindole and 2-(4-carbamidophenoxy)-ethylamine | 18 | 160–165 (ethyl acetate) |
| (h) 2-ethoxycarbonyl-4-[2-hydroxy-3-(benzo[b]-1,4-dioxan-2-yl-methyl-amino)-propoxy]-6-methylindole from 2-ethoxycarbonyl-4-(2,3-epoxy-propoxy)-6-methylindole and 2-(aminomethyl)-1,4-benzo[b]-dioxan | 25 | 135–137 (diethyl ether) |

EXAMPLE 22

4-[2-Hydroxy-3-(3-phenylpropylamino)-propoxy]-indazole 5 g. 4-(2,3-epoxypropoxy)-indazole and 25 g. 3-phenylpropylamine are stirred for 20 hours at 50° C. Excess amine is then distilled off in a vacuum and the residue is triturated with diethyl ether, filtered off with suction and recrystallized from ethyl acetate. There are obtained 4.3 g. (50% of theory) 4-[2-hydroxy-3-(3-phenylpropylamino)-propoxy]-indazole; m.p. 122°–124° C.

EXAMPLE 23

4-{2-Hydroxy-3-[(1-methyl-2-phenoxy)-ethylamino]-propoxy}-indazole 5 g. 4-(2,3-Epoxypropoxy)-indole and 4.17 g. 1-methyl-2-phenoxyethyl)-amine are heated in 10 ml. 1,2-dimethoxyethane for 20 hours at 50° C. After trituration with acetone, suction filtration and recrystallization from isopropanol, there are obtained 3.7 g. (41% of theory) 4-{2-hydroxy-3-[(1-methyl-2-phenoxy)-ethylamino]-propoxy}-indazole; m.p. 175°–177° C.

EXAMPLE 24

2-Benzyl-4-{2-hydroxy-3-[2-(3,4-dimethoxyphenyl)-ethylamino]-propoxy}-indazole 17 g. 2-Benzyl-4-(2,3-epoxypropoxy)-indazole and 20 g. 2-(3,4-dimethoxyphenyl)-ethylamine are stirred for 20 hours at 70° C. Excess amine is dissolved by stirring with diethyl ether, followed by suction filtration. There are obtained 19.1 g. (74% of theory) 2-benzyl-4-{2-hydroxy-3-[2-(3,4-dimethoxyphenyl)-ethylamino]-propoxy}-indazole; m.p. 101°–102° C.

EXAMPLE 25

The following compound is obtained in a manner analogous to that described in Example 24:

| designation | yield % of theory | m.p. °C. (solvent) |
|---|---|---|
| 2-benzyl-4-{2-hydroxy-3-[2-(2-benzyloxyphenoxy)-ethylamino]-propoxy{-indazole from 2-benzyl-4-(2,3-epoxypropoxy)-indazole and 2-(2-benzyloxy-phenoxy)-ethylamine | 91 | 81–83 (ethanol) |

EXAMPLE 26

2-Benzyl-4-[2-hydroxy-3-(2-phenoxyethylamino)-propoxy]-indazole 5 g. 2-Benzyl-4-(2,3-epoxypropoxy)-indazole and 2.6 g. 2-phenoxyethylamine are heated for 48 hours to 50° C. in 10 ml. 1,2-dimethoxyethane. The reaction mixture is then evaporated and the residue is dissolved in methylene chloride and purified chromatographically over a column of silica gel, using methylene chloride/ethyl acetate (8:2 v/v) and ethyl acetate as elution agents. After evaporation, there are obtained 4.2 g. (56% of theory) 2-benzyl-4-[2-hydroxy-3-(2-phenoxyethylamino)-propoxy]-indazole in the form of a viscous oil.

EXAMPLE 27

The following compounds are obtained in a manner analogous to that described in Example 26:

| designation | yield % of theory | m.p. °C. (solvent) |
|---|---|---|
| (a) 2-benzyl-4-{2-hydroxy-3-[2-(2-methoxy-phenoxy)-ethylamino]-propoxy}-indazole from 2-benzyl-4-(2,3-epoxypropoxy)-indazole and 2-(2-methoxy- | 52 | oil |

-continued

| designation | yield % of theory | m.p. °C. (solvent) |
|---|---|---|
| phenoxy)-ethylamine | | |
| (b) 2-benzyl-4-{2-hydroxy-3-[2-(2-methoxy-phenoxy)-propylamino]-propoxy}-indazole from 2-benzyl-4-(2,3-epoxypropoxy)-indazole and 2-(2-methoxy-phenoxy)-propylamine | 83 | oil |
| (c) 2-benzyl-4-{2-hydroxy-3-[2-(4-pyridyl)-ethylamino]-propoxy}-indazole from 2-benzyl-4-(2,3-epoxypropoxy)-indazole and 2-(4-pyridyl)-ethylamine | 51 | oil |
| (d) 2-benzyl-4-[2-hydroxy-3-(benzo-[b]-1,4-dioxan-2-yl-methyl-amino)-propoxy]-indazole from 2-benzyl-4-(2,3-epoxypropoxy)-indazole and 2-(aminomethyl)-1,4-benzo[b]-dioxan | 47 | oil |
| (e) 2-benzyl-4-{2-hydroxy-3-[2-(3,4-ethylenedioxyphenyl)-ethylamino]-propoxy}-indazole from 2-benzyl-4-(2,3-epoxypropoxy)-indazole and 2-(3,4-ethylene-dioxyphenyl)-ethylamine | 76 | 165—168 (isopropanol) |
| (f) 2-benzyl-4-{2-hydroxy-3-[2-(3-ethoxy-4-methoxyphenyl)-ethylamino]-propoxy}-indazole from 2-benzyl-4-(2,3-epoyxpropoxy)-indazole and 2-(3-ethoxy-4-methoxyphenyl)-ethylamine | 85 | oil |
| (g) 2-benzyl-4-{2-hydroxy-3-[2-(3,4,5-trimethoxyphenyl)-ethylamino]-propoxy}-indazole from 2-benzyl-4-(2,3-epoxypropoxy)-indazole and 2-(3,4,5-trimethoxyphenyl)-ethylamine | 88 | oil |
| (h) 2-benzyl-4-(2-hydroxy-3-[2-(4-benzyloxy-3-methoxyphenyl)-ethylamino]-propoxy}-indazole from 2-benzyl-4-(2,3-epoxypropoxy)-indazole and 2-(benzyloxy-3-methoxyphenyl)-ethylamine | 78 | 96–98 (methanol) |
| (i) 2-benzyl-4-{2-hydroxy-3-[2-(3-benzyloxy-4-butoxyphenyl)-ethylamino]-propoxy}-indazole from 2-benzyl-4-(2,3-epoxypropoxy)-indazole and 2-(3-benzyloxy-4-butoxyphenyl)-ethylamine | 80 | oil |
| (j) 2-benzyl-4-{2-hydroxy-3-[2-(3,4-dibenzyloxyphenyl)-ethylamino]-propoxy}-indazole from 2-benzyl-4-(2,3-epoxypropoxy)-indazole and 2-(3,4-dibenzyloxy-phenyl)-ethylamine | 84 | oil |
| (k) 2-benzyl-4-{2-hydroxy-3-[2-(2-pyridoxy)-ethylamino]-propoxy}-indazole from 2-benzyl-4-(2,3-epoxypropoxy)-indazole and 2-(2-pyridoxy)-ethylamine | 64 | oil |

EXAMPLE 28

2-Benzyl-4-{2-hydroxy-3-[2-(2-hydroxyphenoxy)-N-benzylpropylamino]-propoxy}-indazole 4.2 g. 2-Benzyl-4-(2,3-epoxypropoxy)-indazole and 3.85 g. 2-(2-hydroxyphenoxy)-N-benzylpropylamine are boiled under reflux for 4 days in 30 ml. dioxan under an atmosphere of nitrogen. The reaction mixture is then evaporated, the residue is dissolved in methylene chloride and then purified chromatographically over a column of silica gel. After evaporation of the eluate, there are obtained 5.8 g. (72% of theory) 2-benzyl-4-{2-hydroxy-3-[2-(2-hydroxyphenoxy)-N-benzyl-propylamino]-propoxy}-indazole in the form of a viscous oil.

EXAMPLE 29

The following compound is obtained in a manner analogous to that described in Example 28:

| designation | yield % of theory | m.p. °C. (solvent) |
|---|---|---|
| 2-benzyl-4-{2-hydroxy-3-[2-(4-acetamidophenoxy)-N-benzyl-ethylamino]-propoxy}-indazole from 2-benzyl-4-(2,3-epoxypropoxy)-indazole and 2-(4-acetamido-phenoxy)-N-benzylethylamine | 67 | oil |

The 2-benzyl-4-(2,3-epoxypropoxy)-indazole used as starting material can be prepared as follows:

9.2 g. sodium hydride (55–60% suspension in paraffin) are introduced, with cooling and under an atmosphere of nitrogen, into a solution of 47.1 g. 2-benzyl-4-hydroxyindazole in 250 ml. dimethylformamide. After the ending of the evolution of nitrogen, 19 ml. epibromohydrin are added dropwise thereto, followed by stirring for 16 hours at ambient temperature. Thereafter, the reaction mixture is stirred into 1.5 liters water, extracted with methylene chloride and purified over a column of silica gel, using methylene chloride/methanol (99:1 v/v) as elution agent. After trituration with ligroin:diethyl ether (1:1 v/v) and suction filtration, there are obtained 30 g. (51% of theory) 2-benzyl-4-(2,3-epoxypropoxy)-indazole; m.p. 66°–68° C.

EXAMPLE 30

4-{2-Hydroxy-3-[2-(3,4-dimethoxyphenyl)-ethylamino]-propoxy}-indazole 19.1 g. 2-Benzyl-4-{2-hydroxy-3-[2-(3,4-dimethoxyphenyl)-ethylamino]-propoxy}-indazole (preparation see Example 24) are hydrogenated in 700 ml. methanol and 22.4 ml. concentrated hydrochloric acid in the presence of 2 g. 10% palladium-charcoal. After filtering with suction, the filtrate is evaporated and the residue is dissolved in water, rendered alkaline with aqueous sodium hydroxide solution and extracted with methylene chloride. The organic phase is evaporated and the residue is triturated with diethyl ether and filtered with suction. There are obtained 9.1 g. (59% of theory) 4-{2-hydroxy-3-[2-(3,4-dimethoxyphenyl)-ethylamino]-propoxy}-indazole; m.p. 118°–119° C.

The corresponding hydrochloride (m.p. 157°–159° C.) is obtained by dissolving the base in ethanol and adding ethereal hydrochloric acid.

The following compounds are obtained in an analogous manner:

| designation | Yield % of theory | m.p. 20 C. (solvent) |
|---|---|---|
| (a) 4-{2-hydroxy-3-[2-(2-hydroxyphenoxy)-ethylamino]-propoxy}-indazole from 2-benzyl-4-{2-hydroxy-3-[2-(2-benzyloxyphenoxy)-ethylamino]-propoxy}-indazole (see Example 25) | 41 | 137–139 (isopropanol) |
| (b) 4-[2-hydroxy-3-(2-phenoxyethylamino)-propoxy]-indazole from 2-benzyl-4-[2-hydroxy-3-(2-phenoxyethylamino)-propoxy]-indazole (see Example 26) | 88 | 134–135 (ethyl acetate) |
| (c) 4-{2-hydroxy-3-[2-(2-methoxyphenoxy)-ethylamino]-propoxy}-indazole from 2-benzyl-4-{2-hydroxy-3-[2-(2-methoxyphenoxy)-ethylamino]-propoxy}-indazole (see Example 27a) | 82 | 106–107 (ethyl acetate) |
| (d) 4-{2-hydroxy-3-[2-(2-methoxyphenoxy)-propylamino]-propoxy}-indazole from 2-benzyl-4-{2-hydroxy-3-[2-(2-methoxyphenoxy)-propylamino]-propoxy}-indazole (see Example 27b) | 58 | 127–128 (ethyl acetate) |
| (e) 4-{2-hydroxy-3-[2-(4-pyridyl)-ethylamino]-propoxy}-indazole from 2-benzyl-4-{2-hydroxy-3-[2-(4-pyridyl)-ethylamino]-propoxy indazole (see Example 27c) | 72 | 123–125 (ethyl acetate) |
| (f) 4-[2-hydroxy-3-(benzo[b]-1,4-dioxan-2-yl-methylamino)-propoxy]-indazole from 2-benzyl-4-[2-hydroxy-3-(benzo-[b]-1,4-dioxan-2-yl-methylamino)-propoxy]-indazole (see Example 27d) | 54 | 142–143 (ethyl acetate) |
| (g) 4-{2-hydroxy-3-[2-(2-hydroxy phenoxy)-propylamino]-propoxy}-indazole from 2-benzyl-4-{2-hydroxy-3-[2-(2-hydroxyphenoxy)-N-benzylpropylamino]-propoxy}-indazole (see Example 28) | 57 | 92–95 (ethyl acetate) |
| (h) 4-{2-hydroxy-3-[2-(4-acetamidophenoxy)-ethylamino]-propoxy}-indazole from 2-benzyl-4-{2-hydroxy-3-[2-(4-acetamidophenoxy)-N-benzylethylamino]-propoxy}-indazole (see Example 29) | 49 | 130–133 (ethanol/water) |
| (i) 4-{2-hydroxy-3-[2-(3,4-ethylenedioxyphenyl)-ethylamino]-propoxy}-indazole from 2-benzyl-4-{2-hydroxy-3-[2-(3,4-ethylenedioxyphenyl)-ethylamino]-propoxy}-indazole (see Example 27e) | 59 | 125–126 (ethyl acetate) |
| (j) 4-{2-hydroxy-3-[2-3-ethoxy-4-methoxyphenyl)-ethylamino]-propoxy}-indazole from 2-benzyl-4-{2-hydroxy-3-[2-(3-ethoxy-4-methoxyphenyl)-ethylamino]-propoxy}-indazole (see Example 27f) | 73 | 118–119 (ethyl acetate) |
| (k) 4-{2-hydroxy-3-[2-(3,4,5-trimethoxyphenyl)-ethylamino]-propoxy}-indazole from 2-benzyl-4-{2-hydroxy-3-[2-(3,4,5-trimethoxyphenyl)-ethylamino]-propoxy}-indazole (see Example 27g) | 63 | 171–172 (ethyl acetate) |
| (l) 4-{2-hydroxy-3-[2-(4-hydroxy-3-methoxyphenyl)-ethylamino]-propoxy}-indazole from 2-benzyl-4-{2-hydroxy-3-[2-(4-benzyloxy-3-methoxyphenyl)-ethylamino]-propoxy}-indazole (see Example 27h) | 57 | 139–141 (isopropanol/ethyl acetate) |
| (m) 4-{2-hydroxy-3-[2-(4-butoxy-3-hydroxyphenyl)-ethylamino]-propoxy}-indazole from 2-benzyl-4-{2-hydroxy-3-[2-(3-benzyloxy-4-butoxyphenyl)-ethylamino]-propoxy}-indazole (see Example 27i) | 55 | 94–97 (ethyl acetate) |
| (n) 4-{2-hydroxy-3-[2-(3,4-dihydroxyphenyl)-ethylamino]-propoxy}-indazole acetate from 2-benzyl-4-{2-hydroxy-3-[2-(3,4-dibenzyloxyphenyl)-ethylamino]-propoxy}-indazole (see Example 27j) | 46 | 160–162 (ethanol) |
| (o) 4-{2-hydroxy-3-[2-(2-pyridyloxy)-ethylamino]-propoxy}-indazole from 2-benzyl-4-{2-hydroxy-3-[2-(2-pyridoxy)-ethylamino]-propoxy}-indazole (see Example 27k) | 52 | 113–115 (ethyl acetate) |

EXAMPLE 31

4-{2-Hydroxy-3-[1-(3,4-dimethoxyphenyl)-propyl-2-amino]-propoxy}-indazole

A mixture of 4 g. 2-benzyl-4-(3-amino-2-hydroxypropoxy)-indazole and 3 g. 3,4-dimethoxyphenylacetone is hydrogenated in 100 ml. methanol in the presence of 1.5 g. 10% palladium-charcoal. After the take up of 1 mol hydrogen, 10 ml. concentrated hydrochloric acid are added thereto and the reaction mixture shaken until a further 1 mol hydrogen is taken up.

The reaction mixture is filtered with suction and evaporated and the residue is taken up in water and methylene chloride. After separation of the aqueous phase, it is rendered alkaline and extracted with methylene chloride/methanol (10:1 v/v). After drying the extract and evaporating, the diastereomeric mixture obtained is recrystallized from ethyl acetate. There is thus obtained 1.1 g. (21% of theory) of fraction A of 4-{2-hydroxy-3-[1-(3,4-dimethoxyphenyl)-propyl-2-amino]-propoxy}-indazole; m.p. 110°–112° C.

By evaporation of the mother liquor and trituration of the residue with diethyl ether, there is obtained, after suction filtration, 1.5 g. (29% of theory) of fraction B of 4-{2-hydroxy-3-[1-(3,4-dimethoxyphenyl)-propyl-2-amino]-propoxy}-indazole; m.p. 66°–73° C.

The 2-benzyl-4-(3-amino-2-hydroxypropoxy)-indazole used as starting material can be obtained as follows:

12 g. 2-Benzyl-4-(2,3-epoxypropoxy)-indazole are shaken in an autoclave in 100 ml. liquid ammonia for 8 hours at 50° C. After taking up with ethyl acetate, filtering with suction and subsequently washing, there are obtained 9.3 g. (73% of theory) 2-benzyl-4-(3-amino-2-hydroxypropoxy)-indole; m.p. 113°–115° C.

EXAMPLE 32

4-{2-Hydroxy-3-[3-(3,4-dimethoxyphenyl)-propylamino]-propoxy}-indazole benzoate 6.6 g. 4-(3-Amino-2-hydroxypropoxy)-indazole (crude product) in 80 ml. methylene chloride are stirred for 48 hours at ambient temperature in the presence of 3.1 ml. triethylamine with 5.1 g. 3-(3,4-dimethoxyphenyl)-propionyl chloride. After shaking out the reaction mixture with water, drying and evaporating, there are obtained 9.1 g. 4-{2-hydroxy-3-[3-(3,4-dimethoxyphenyl)-propionamido]-propoxy}-indole; m.p. 148°–150° C., after recrystallization from nitromethane.

The crude product thus obtained is stirred in 120 ml. anhydrous tetrahydrofuran with 1.7 g. lithium aluminium hydride under an atmosphere of nitrogen for 26 hours at 60° C. After the usual decomposition and working up, the oil obtained is purified over a column of silica gel, using ethyl acetate:methanol (9:1–6:4 v/v) as elution agent. After evaporation of the desired fractions, 1.7 g. of colorless oil is obtained. By dissolving in ethanol and adding the calculated amount of benzoic acid, followed by evaporation and the addition of diethyl ether, there is obtained 1.75 g. (15% of theory) 4-{2-hydroxy-3-[3-(3,4-dimethoxyphenyl)-propylamino]-propoxy}-indazole benzoate; m.p. 131°–134° C.

The 4-(3-amino-2-hydroxypropoxy)-indazole used as starting material can be obtained as follows:

5.1 g. 1-Acetyl-4-(3,4-epoxypropoxy)-indazole, dissolved in 50 ml. methanol, are stirred in an autoclave with 250 ml. liquid ammonia for 8 hours at 50° C. The solution obtained is treated with active charcoal, evaporated to give 6.6 g. 4-(3-amino-2-hydroxypropoxy)-indazole which, without further purification, can be used in the next step.

EXAMPLE 33

1-Pivaloyl-4-{2-pivaloyloxy-3-[2-(3,4-dimethoxyphenyl)-ethylamino]-propoxy}-indazole hydrochloride A mixture of 4.2 g. 4-{2-hydroxy-3-[2-(3,4-dimethoxyphenyl)-ethylamino]-propoxy}-indazole hydrochloride (preparation see Example 30), 4.2 ml. pivalic anhydride and 35 ml. pivalic acid is stirred for 50 to 60 hours at 75° C. The solid mass obtained is stirred with ligroin, filtered off with suction and washed with ligroin. There are obtaied 4.1 g. (69% of theory) 1-pivaloyl-4-{2-pivaloyloxy-3-[2-(3,4-dimethoxyphenyl)-ethylamino]-propoxy}-indazole hydrochloride; m.p. 155°–158° C.

EXAMPLE 34

4-{2-Pivaloyloxy-3-[2-(3,4-dimethoxyphenyl)-ethylamino]-propoxy}-indazole 4.0 g. 1-Pivaloyl-4-{2-pivaloyloxy-3-[2-(3,4-dimethoxyphenyl)-ethylamino]-propoxy}-indazole hydrochloride (preparation see Example 33) are heated under reflux for 2.5 hours with 150 ml. isopropylamine. The reaction mixture is evaporated and the residue is dissolved in diethyl ether and shaken with 1 N aqueous sodium hydroxide solution. The organic phase is then purified chromatographically over a column of silica gel, using methylene chloride:ethyl acetate (1:1 v/v) as elution agent. There are obtained 2.7 g. (85% of theory) 4-{2-pivaloyloxy-3-[2-(3,4-dimethoxyphenyl)-ethylamino]-propoxy}-indazole in the form of an oil.

EXAMPLE 35

4-{2-Hydroxy-3-[2-(3,4-dimethoxyphenyl)-ethylamino]-propoxy}-1-formylindoline benzoate 2.2 g. 4-(2,3-Epoxypropoxy)-1-formylindoline and 1.8 g. 2-(3,4-dimethoxyphenyl)-ethylamine are stirred at ambient temperature for 18 hours in 50 ml. n-butanol. The reaction mixture is then evaporated in a vacuum and the residue taken up in diethyl ether and 1 N lactic acid. The aqueous phase is rendered alkaline with 2 N aqueous sodium hydroxide solution and extracted with methylene chloride. After drying and evaporating, there are obtained 4 g. of crude product. This is purified over a column of silica gel, using methylene chloride/methanol (95:5 v/v) as elution agent, 1.3 of base thus being obtained. This is dissolved in 50 ml. ethyl acetate and mixed with the equivalent amount of benzoic acid. After suction filtration, there is obtained 1.3 g. (24% of theory) 4-{2-hydroxy-3-[2-(3,4-dimethoxyphenyl)-ethylamino]-propoxy}-1-formylindoline benzoate; m.p. 136°–138° C.

EXAMPLE 36

The following compounds are obtained in a manner analogous to that described in Example 35:

| designation | Yield % of theory | m.p. °C. (solvent) |
| --- | --- | --- |
| (a) 4-{2-hydroxy-3-[2-(4-fluoro-phenoxy)-ethylamino]-propoxy}-1-formylindoline benzoate from 4-(2,3-epoxypropoxy)-1-formyl-indoline and 2-(4-fluorophenoxy)-ethylamine | 20 | 121–123 (ethyl acetate) |
| (b) 4-{2-hydroxy-3-[2-(2-methoxy-phenoxy)-ethylamino]-propoxy}-1-formylindoline benzoate from 4-(2,3-epoxypropoxy)-1-formyl-indoline and 2-(2-methoxyphenoxy)-ethylamine | 19 | 78–79 (ethyl acetate) |
| (c) 4-{2-hydroxy-3-[2-(2-methoxy-phenoxy)-N-benzylpropylamino]-propoxy}-1-formylindoline from 4-(2,3-epoxypropoxy)1-formyl-indoline and 2-(2-methoxyphenoxy)-N-benzylpropylamine | 90 | oil |
| (d) 4-{2-hydroxy-3-[2-(2-benzyloxy-phenoxy) N-benzylethylamino]-propoxy}-1-formylindoline from 4-(2,3-epoxypropoxy)-1-formyl-indoline and 2-(2-benzyloxy-phenoxy)-N-benzylethylamine | 95 | oil |
| (e) 4-[2-hydroxy-3-(2-phenylethyl-amino)-propoxy]-1-formylindoline from 4-(2,3-epoxypropoxy)-1-formyl-indoline and 2-phenylethylamine | 18 | 121–123 (ethyl acetate) |
| (f) 4-{2-hydroxy-3-[2-(2-chloro-phenoxy)-ethylamino]-propoxy}-1-formylindoline from 4-(2,3-epoxypropoxy)-1-formyl-indoline and 2-(2-chlorophenoxy)-ethylamine | 15 | 104–107 (ethyl acetate) |
| (g) 4-{2-hydroxy-3-[2-(2-methylthio-phenoxy)-ethylamino]-propoxy}-1-formylindoline from | 20 | 129–130 (methanol) |

| designation | Yield % of theory | m.p. °C. (solvent) |
|---|---|---|
| 4-(2,3-epoxypropoxy)-1-formyl-indoline and 2-(methylthiophenoxy)-ethylamine | | |

EXAMPLE 37

4-{2-Hydroxy-3-[2-(2-methoxyphenoxy)-propylamino]-propoxy}-1-formylindoline benzoate 6.7 g. 4-{2-hydroxy-3-[2-(2-methoxyphenoxy)-N-benzylpropylamino]-propoxy}-1-formylindoline (preparation see Example 36c) are hydrogenated in 250 ml. ethanol and 20 ml. triethylamine at ambient temperature and 1 bar hydrogen pressure over 2 g. 10% palladium-charcoal. The reaction mixture is filtered and the filtrate is evaporated. The residue obtained is dissolved in 50 ml. ethyl acetate and mixed with an equivalent amount of benzoic acid. After suction filtration, there are obtained 2.1 g. (31% of theory) 4-{2-hydroxy-3-[2-(2-methoxyphenoxy)-propylamino]-propoxy}-1-formylindoline benzoate; m.p. 131°-133° C.

EXAMPLE 38

The following compound is obtained in a manner analogous to that described in Example 37:

| designation | Yield % of theory | m.p. °C. (solvent) |
|---|---|---|
| 4-{2-hydroxy-3-[2-(2-hydroxy-phenoxy)-ethylamino]-propoxy}-1-formylindoline acetate from 4-{2-hydroxy-3-[2-(2-benzyloxy-phenoxy)-N-benzylethylamino]-propoxy}-1-formylindoline (see Example 36d) | 41 | 171–173 (ethyl acetate) |

The starting material used for the preparation of the above compound can be obtained as follows:

4-(2,3-Epoxypropoxy)-1-formylindoline 48.6 g. 2-Benzyloxy-6-nitrotoluene are dissolved in 670 ml. dimethylformamide and mixed with 29.9 g. paraformaldehyde and then 200 ml. 1 N potassium tert-.butylate solution added thereto dropwise. After stirring for 1 hour at ambient temperature, the reaction mixture is stirred into 3 liters ice water and extracted with diethyl ether. The ethereal phase is dried with anhydrous sodium sulphate and evaporated in a vacuum. There are obtained 62 g. 2-benzyloxy-6-nitrophenylethanol, which is used in the next stage as the crude product.

62 g. 2-Benzyloxy-6-nitrophenylethanol are dissolved in 500 ml. anhydrous pyridine and, while cooling to about 10° C., mixed with 47.7 g. p-toluenesulphonyl chloride. The temperature of the reaction mixture is allowed to increase to ambient temperature and then stirred for about 10 hours until the reaction is complete, whereafter the reaction mixture is stirred into ice water. After suction filtration, washing with water and drying, there are obtained 74 g. 2-(2-benzyloxy-6-nitrophenyl)-ethyl p-toluenesulphonate; m.p. 96°-98° C. The yield is 86% of theory, referred to the 2-benzyloxy-6-nitrotoluene.

74 g. 2-(2-Benzyloxy-6-nitrophenyl)-ethyl p-toluenesulphonate are dissolved in 2 liters ethylene glycol monomethyl ether, mixed with 5 g. 10% palladium-charcoal and then hydrogenated at ambient temperature and 1 bar hydrogen pressure. After filtering off the catalyst, the filtrate is evaporated and the residue is formylated with a mixture of 227 ml. acetic anhydride and 91 ml. formic acid (see C. W. Huffmann, J. org. Chem., 23, 727/1958). After the reaction is complete, the reaction mixture is decomposed with ice water and extracted with ethyl acetate. The organic phase is neutralised, dried with anhydrous sodium sulphate and evaporated in a vacuum. The residue obtained is mixed with 320 ml. epichlorohydrin and then with 173 ml. 2 N sodium methylate solution. After stirring overnight, the reaction mixture is evaporated and the residue is dissolved in water and ethyl acetate. From the evaporation residue of the ethyl acetate phase, there are obtained, by trituration with isopropanol and suction filtration, 15.8 g. (42% of theory) 4-(2,3-epoxypropoxy)-1-formylindoline; m.p. 88°-89° C.

EXAMPLE 39

Tablets are prepared, each of which contains 10 mg. 4-{2-hydroxy-3-[2-(2-methoxyphenoxy)-ethylamino]-propoxy}-7-methyl-2-benzimidazolinone hydrochloride. The tablets are prepared according to the following formulation:

| | |
|---|---|
| 4-{2-hydroxy-3-[2-(2-methoxyphenoxy)-ethylamino]-propoxy}-7-methyl-2-benzimidazolinone hydrochloride | 10 g. |
| lactose | 80 g. |
| starch | 29 g. |
| magnesium stearate | 1 g. |

The active compound is finely powdered and mixed with the lactose and starch. The mixture is then granulated in the usual manner, magnesium stearate is added to the granulate and the mixture is pressed to give 1000 tablets, each with a weight of 0.12 g.

EXAMPLE 40

In a manner analogous to that described in example 23 there are obtained the following compounds:

| | designation | Yield % of theory | m.p. °C. (solvent) |
|---|---|---|---|
| (a) | 4-{2-hydroxy-3-[2-(2-allylphenoxy)-ethylamino]-propoxy}-indazole from 4-(2,3-epoxypropoxy)-indozole and 2-(2-Allylphenoxy)-ethylamine | 47 | 125–126 ethyl acetate |
| (b) | 4-{2-hydroxy-3-[2-(2-allyloxyphenoxy) ethylamimo]-propoxy}-indazole from 4-(2,3-epoxypropoxy)-indazole and 2-(2-Allyloxyphenoxy)-ethylamine | 45 | 137–139 ethyl acetate |

The effectiveness of the compounds of the invention as vaso-dilators and beta-receptor blocking agents are illustrated by the following tests:

A-Vaso Dilator Experiments

Rabbits were anesthesized with urethane and a catheter implanted in the middle ear artery (A. femoralis) for a continuous measurement of their arterial blood pressure. The blood pressure measurements were effected using an electromechanical transducer (Statham P 23 Dd) and were recorded in a direct printer and utilized after calibration with a mercury manometer.

After determination of the starting value both jugular arteries (A. carotis) were occluded for two minutes and blood pressure thereby temporarily increased (CSE-reflex). The test compound was then injected at the lowest experimental dosage (0.125 mg/kg) intravenously and eight minutes later the CSE-reflex was again induced. In intervals of 15 minutes, the test compound was again injected in logarithmically increased dosage (Factor 2) and the CSE-reflex again induced.

Test compounds which under these conditions moderated the CSE-induced blood pressure increase were demonstrated to be vaso-dilators and the dosage which decreased the CSE-reflex by 30 mm Hg was determined (designated as $DE_{-30}$ mm Hg in the table below).

B-Beta Receptor Blocking Activity Experiments

The heart beat frequency of rabbits was monitored via implanted electrode and recorded on a frequency counter having a measurement time of 15 seconds. Isoprenalin was then injected intravenously via an ear vein, inducing an increase in hear beat frequency of from ca. 210 beats/min. to 370 beats/min. Subequently, the test compounds were administered in increased dosage (as in Experiment A) intravenously and the heart frequency increase after isoprenalin treatment again recorded. The inhibition of isoprenalin tachycardia was taken as a measure of the beta-blockage activity of the test compounds. The dosage which reduced the isoprenalin increase by 50% was determined for each test substance and is hereinafter designated as $HD_{50}$.

The results from the above experiments A and B are set forth in the table below. The determination of the equal effectiveness dosages, i.e., $DE_{-30}$ mm Hg and $HD_{50}$, were determined on a logarithmic basis from four to six individual experiments and then the quotient of the beta-blockage dosage $HD_{50}$ to the vaso dilating dosage ($DE_{-30}$ mm Hg) was calculated.

All of the test substances reported below are strong beta-blockers and additionally exhibit a pronounced blood pressure depressant properties. Since both effects are desired, it is advantageous to find both effects at dosages which are as close together as possible since otherwise the efficacy of one or the other effect would be reduced because of under-dosing. Accordingly, rations of $HD_{50}/DE_{-30}$ mm Hg of very approprimately are desirable.

| Vaso-Dilating and Beta-blocking Activity of Inventive Compounds In Comparison to Propranolol* | | | |
|---|---|---|---|
| Example No. | $ED_{-30mmHg}$ (vaso-dial. Act) (μg/kg i.v.) | $HD_{50}$ (B-blocking Act.) (μg/kg i.v.) | $\dfrac{HD_{50}}{ED_{-30mmHg}}$ |
| 2d | 641 | 406 | 0,63 |
| 3 | 1410 | 2485 | 1,76 |
| 4a | 3420 | 762 | 0,22 |
| 4b | 1910 | 3460 | 1,81 |
| 4c | 2240 | 5222 | 2,33 |
| 4f | 1660 | 931 | 0,51 |
| 4h | 3170 | 1338 | 0,42 |
| 4i | 5790 | 4338 | 0,75 |
| 7 | 3060 | 544 | 0,18 |
| 11 | 1160 | 233 | 0.20 |
| 15 | 400 | 59 | 0,15 |
| 16a | 1359 | 160 | 0,12 |
| 16b | 1580 | 487 | 0,31 |
| 16c | 1920 | 569 | 0,30 |
| 16e | 280 | 105 | 0,38 |
| 18c | 420 | 252 | 0,60 |
| 30f | 1980 | 154 | 0,21 |
| 34 | 3780 | 1253 | 0,33 |
| 36b | 1620 | 991 | 0,61 |
| Propranolol | | 393 | |

*The comparison substance propranolol is 1-isopropylamino-3-(-1-naphthyloxy)-2-propanol The results indicate that the inventive compounds exhibit substantially greater beta-blocking activity than the prior art material.

In actual administration of the inventive compounds, e.g., in the treatment of hypertension or angina pectoris, the appropriate dosage is of course dependent on the condition of the patient and the specific infirmity to be treated. In general, treatment should begin with small doses (e.g., 100 mg) and increased gradually depending upon the patient's response. The dosage can be increased at 5 to 7 day intervals until an average daily dosage of 100 to 300 mg is reached. For maintenance, 2 to 4 doses a day are usually required. These dosage levels will generally be appropriate, both for achieving a vaso dilating effect, i.e., for reducing blood pressure, and for inhibition of adrenergic beta-receptor activity.

The present invention provides pharmaceutical compositions which contain at least one of the new compounds in admixture with a solid or liquid pharmaceutical diluent or carrier and, if desired, also with odoriferous, flavoring and/or coloring materials, followed by forming into, for example, tablets or dragees or, with the addition of appropriate adjuvants, suspended or dissolved in water or oil, for example olive oil.

It will be understood that the specification and examples are illustrative, but not limitative of the present invention and that other embodiments within the spirit and scope of the invention will suggest themselves to those skilled in the art.

What is claimed is:

1. Heterocylic oxypropanol compounds of the formula

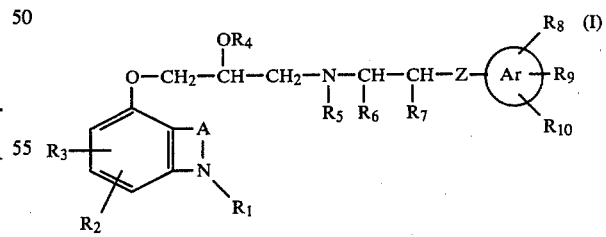

wherein
$R_1$, $R_2$, $R_6$ and $R_7$ are individually selected from hydrogen or lower alkyl with 1 to 6 carbon atoms;
$R_3$, $R_4$, $R_5$ and $R_{10}$ are each hydrogen
Z is a valency bond or oxygen;
Ar is phenyl;
$R_8$, $R_9$ are identical or different, hydrogen, alkyl with up to 6 carbon atoms, alkenyl with up to 6 carbon atoms, allyloxy, alkylthio with up to 6 carbon atoms, alkanoylamino in which the alkanoyl component contains up to 8 carbon atoms, alkanoylamino in which the alkanoyl component contains up to 8 carbon atoms, alkanoyl with up to 8 carbon atoms, aminocarbonyl or benzyloxy; and A is -N=N-.

2. Heterocyclic oxypropanol compound as claimed in claim 1 wherein $R_1$ is hydrogen.

3. Heterocyclic oxypropanol compound as claimed in claim 1 wherein $R_1$ is lower alkyl.

4. Heterocyclic oxypropanol compound as claimed in claim 1 wherein $R_2$ and $R_3$ are both hydrogen.

5. Heterocyclic oxypropanol compound as claimed in claim 1 wherein $R_6$ is hydrogen.

6. Heterocyclic oxypropanol compound as claimed in claim 1 wherein $R_6$ is lower alkyl.

7. Heterocyclic oxypropanol compound as claimed in claim 1 wherein $R_7$ is hydrogen.

8. Heterocyclic oxypropanol compound as claimed in claim 1 wherein $R_7$ is lower alkyl.

9. Heterocyclic oxypropanol compound as claimed in claim 1 wherein Z is a valency bond.

10. Heterocyclic oxypropanol compound as claimed in claim 1 wherein Z is oxygen.

11. Heterocyclic oxypropanol compound as claimed in claim 1 wherein $R_8$, $R_9$ and $R_{10}$ are hydrogen.

12. Heterocyclic oxypropanol compound designated 4-{2-hydroxy-3-[2-(2-methoxyphenoxy)-ethylamino]-propoxy}-benzotriazole hydrochloride.

13. Method of treating a subject for circulatory and cardiac diseases which comprises administering to an afflicted subject, a pharmacologically effective amount of a heterocyclic oxypropanol compound as claimed in claim 1.

14. Method as claimed in claim 13 wherein the compound is applied at a dosage of 1 to 3 mg/kg daily.

15. Method as claimed in claim 13 wherein such compound is applied in a prophylactic manner.

16. Method as claimed in claim 13 wherein said circulatory and cardiac disease is hypertension.

17. Method as claimed in claim 13 wherein said circulatory and cardiac disease is angina pectoris.

18. Heterocyclic oxypropanol compound as claimed in claim 1 wherein
$R_4$ is hydrogen
Ar is phenyl
$R_5$, $R_6$, $R_7$ are hydrogen and
Z is a valency bond or oxygen.

* * * * *